(12) United States Patent
Avital et al.

(10) Patent No.: US 11,911,373 B2
(45) Date of Patent: Feb. 27, 2024

(54) ATTENTION EVALUATION AND METHODS FOR MEDICATING

(71) Applicant: TECHNION RESEARCH & DEVELOPMENT FOUNDATION LIMITED, Haifa (IL)

(72) Inventors: Avraham Avital, Sarid (IL); Zev Brand, Modiin (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 1215 days.

(21) Appl. No.: 16/541,517

(22) Filed: Aug. 15, 2019

(65) Prior Publication Data

US 2020/0054618 A1 Feb. 20, 2020

Related U.S. Application Data

(60) Provisional application No. 62/719,065, filed on Aug. 16, 2018.

(51) Int. Cl.
| | | |
|---|---|---|
| *A61K 31/4458* | (2006.01) | |
| *A61B 5/16* | (2006.01) | |
| *A61B 5/00* | (2006.01) | |
| *A61B 5/0533* | (2021.01) | |
| *A61B 5/12* | (2006.01) | |

(52) U.S. Cl.
CPC ........ *A61K 31/4458* (2013.01); *A61B 5/0533* (2013.01); *A61B 5/12* (2013.01); *A61B 5/168* (2013.01); *A61B 5/4839* (2013.01)

(58) Field of Classification Search
CPC .................. A61K 31/13; A61K 31/137; A61K 31/4166; A61K 31/4458; A61K 31/496; A61K 31/55; A61K 2300/00; A61B 5/0533; A61B 5/1124; A61B 5/1127; A61B 5/12; A61B 5/162; A61B 5/165; A61B 5/168; A61B 5/377; A61B 5/4839; A61P 25/00; A61P 25/22; A61P 25/24; A61P 25/28

See application file for complete search history.

(56) References Cited

U.S. PATENT DOCUMENTS

| | | | |
|---|---|---|---|
| 8,473,043 B1 * | 6/2013 | Modarres | A61B 5/4848 600/544 |
| 2013/0080185 A1 * | 3/2013 | Picard | A61B 5/0531 705/2 |
| 2014/0243608 A1 * | 8/2014 | Hunt | A61B 5/4848 600/300 |
| 2017/0000400 A1 * | 1/2017 | Gordon | A61B 5/165 |
| 2019/0329063 A1 * | 10/2019 | Hendler | A61K 31/198 |
| 2019/0381017 A1 * | 12/2019 | Guenther | A61K 31/4402 |
| 2019/0381018 A1 * | 12/2019 | Guenther | A61K 9/4841 |
| 2020/0397721 A1 * | 12/2020 | Kortagere | A61K 31/137 |

FOREIGN PATENT DOCUMENTS

WO WO-2016156867 A1 * 10/2016 ........... A61B 5/0002

* cited by examiner

*Primary Examiner* — Orlando Bousono
(74) *Attorney, Agent, or Firm* — The Roy Gross Law Firm, LLC; Roy Gross

(57) ABSTRACT

Provided are methods for diagnosing or selecting a mammal in need of a stimulant ADHD drug, conducting a non-specific electro-dermal responses (EDAs) analysis and/or an auditory sustained attention (ASAT) analysis on the mammal and administering or adjusting the dose of a stimulant ADHD drug to be administered to the mammal.

6 Claims, 23 Drawing Sheets

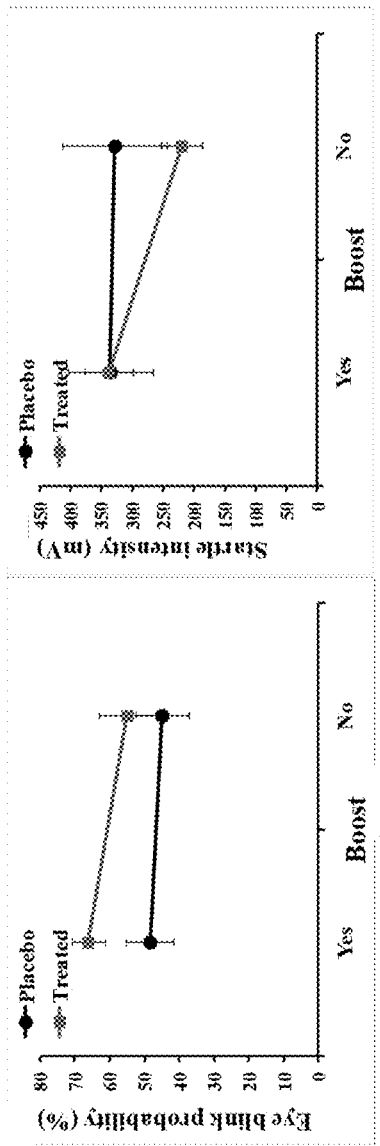
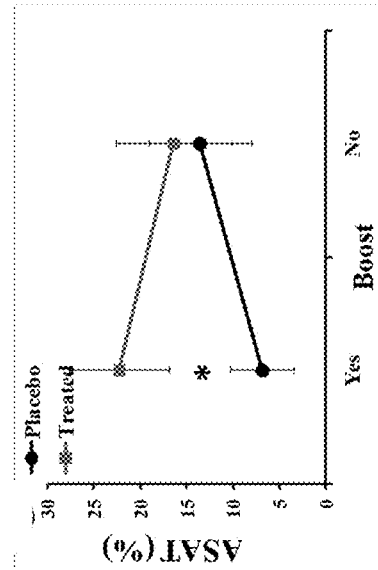
FIG. 10A
FIG. 10B
FIG. 10C

|  | Severity index | | | | Disruption index | | | |
| --- | --- | --- | --- | --- | --- | --- | --- | --- |
|  | Baseline | 2 weeks | 4 weeks | 8 weeks | Baseline | 2 weeks | 4 weeks | 8 weeks |
| Anxiety | .436** | .191 | .395** | .357** | .454** | .213 | .531*** | .453** |
| Memory | .226 | .011 | .290* | .202 | .372** | .007 | .396** | .217 |
| Fatigue | .701*** | .796*** | .737*** | .839*** | .596*** | .679*** | .738*** | .766*** |
| Appetite | .312* | .225 | .141 | .263 | .021 | .115 | .177 | .232 |
| Sleep | .204 | .207 | .244 | .285* | .140 | .162 | .179 | .294* |
| Heat | .300* | -.112 | .213 | .306* | .273* | -.091 | .187 | .305* |

FIG. 11

| | Eye blink probability (%) | | | | Startle intensity (mV) | | | | ASAT (%) | | | |
|---|---|---|---|---|---|---|---|---|---|---|---|---|
| | Baseline | 2 weeks | 4 weeks | 8 weeks | Baseline | 2 weeks | 4 weeks | 8 weeks | Baseline | 2 weeks | 4 weeks | 8 weeks |
| Tumor size | .070 | -.112 | .072 | .001 | -.320* | -.137 | -.093 | -.287* | -.096 | -.090 | -.093 | -.059 |
| BMI | -.270* | -.255 | -.273* | -.128 | -.294* | -.366** | -.083 | -.196 | -.103 | -.118 | -.034 | -.145 |
| Distance from last chemo treatment | -.072 | -.027 | -.064 | .046 | -.117 | -.080 | -.149 | -.110 | -.054 | .178 | -.051 | .209 |

FIG. 12

ATTENTION EVALUATION AND METHODS FOR MEDICATING

CROSS-REFERENCE TO RELATED APPLICATIONS

This application claims the benefit of priority of U.S. Provisional Patent Application No. 62/719,065, filed on Aug. 16, 2018. The contents of the above applications are all incorporated by reference as if fully set forth herein in their entirety.

FIELD OF THE INVENTION

The invention relates generally to the field of evaluating human alertness or attention and predicting the need for a therapy in conditions wherein alertness and/or attention is impaired.

BACKGROUND OF THE INVENTION

Cognitive function, attention and behavioral performance are affected by multiple factors, including sleep deprivation, fatigue, low alertness, and emotional dysregulation. Accordingly, there is a need for new measurement and assessment paradigm instrument that captures the multidimensional nature of alertness as associated with emotional symptoms, which would help identify emotional symptoms in the context of attention deficit disorders.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

In one embodiment, provided herein is a method comprising the steps of: diagnosing or selecting a subject in need of a stimulant ADHD drug; conducting a non-specific electro-dermal responses (EDAs) analysis on the subject; administering the stimulant ADHD drug to the subject having higher value of EDAs compared to a control value.

In a further embodiment, provided herein is a method comprising the steps of: selecting a subject treated with an initial dosage or dose of the stimulant ADHD drug; conducting a non-specific electro-dermal responses (EDAs) analysis on the subject; increasing the initial dose of the stimulant ADHD drug to the subject having higher value of the EDAs compared to a control range/value or maintaining the initial dose of the stimulant ADHD drug to the subject having a value of the EDAs within the control range/value.

In a further embodiment, provided herein is a method comprising the steps of: diagnosing or selecting a subject in need of the stimulant ADHD therapy; conducting an auditory sustained attention (ASAT) analysis on the subject; administering the stimulant ADHD therapy to the subject having lower baseline ASAT performance compared to a control value.

In a further embodiment, provided herein is a method for adjusting a dose of a stimulant ADHD drug, in a subject, comprising the steps of: selecting a subject treated with an initial dosage or dose of the stimulant ADHD drug; conducting an auditory sustained attention (ASAT) analysis on the subject; increasing the initial dose of the stimulant ADHD drug to the subject having lower baseline ASAT performance compared to a control value or maintaining the initial dose of the stimulant ADHD drug to the subject having a baseline ASAT performance within the control range/value.

In a further embodiment, a method as described herein confirms or predicts responsiveness of the subject to the stimulant ADHD drug or to the dosage or dose of the stimulant ADHD drug.

In a further embodiment, a subject having higher value of the EDAs compared to a control value is prone to be responsive to the stimulant ADHD drug.

In a further embodiment, stimulant ADHD drug is selected from: a short-acting stimulant drug, a long-acting stimulant drug, an intermediate-acting stimulant drug, or any combination thereof.

In a further embodiment, a subject having higher value of the EDAs compared to a control value is a subject in need of a dose-increase of the stimulant ADHD drug.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 5A-12 show experimental results in breast cancer patients;

DETAILED DESCRIPTION OF THE INVENTION

Figure 1:
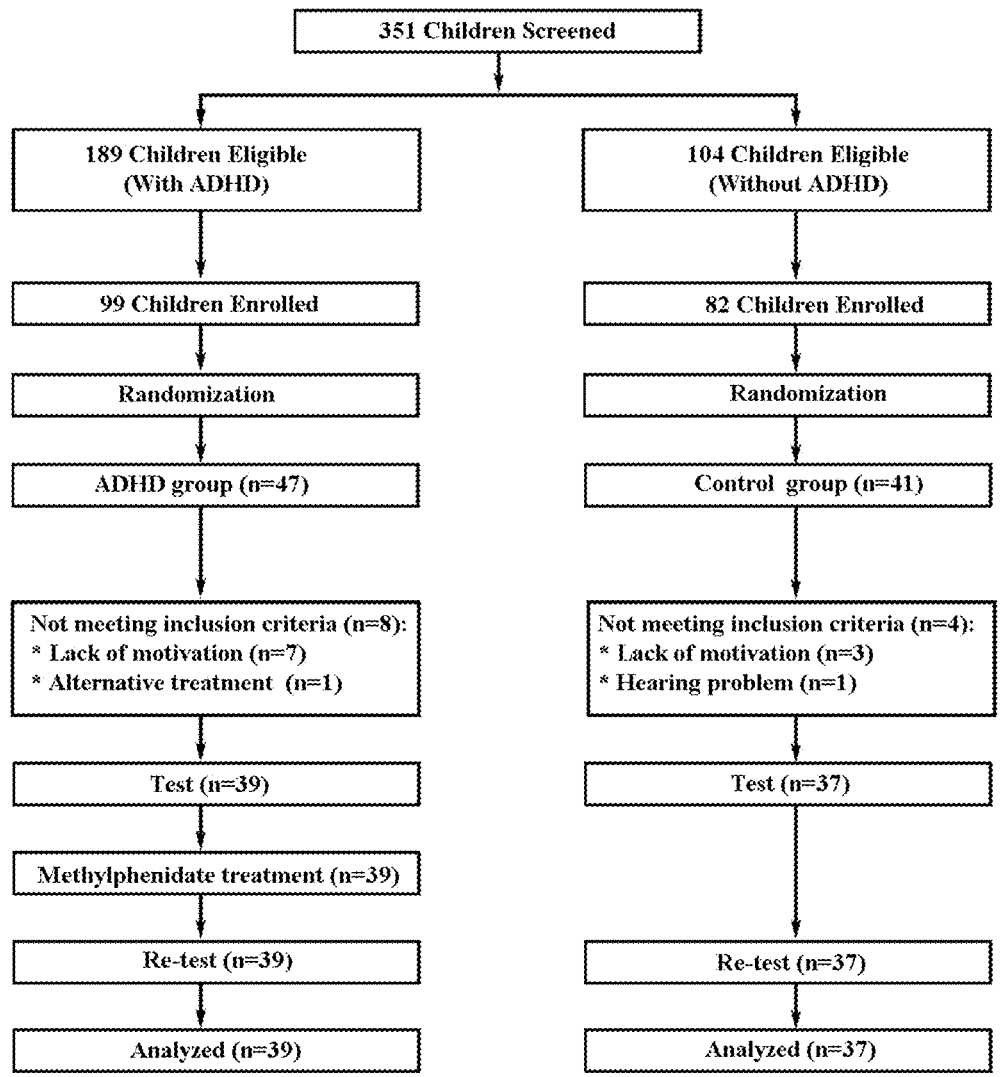
FIG. 1 presents the CONSORT diagram of the flow of participants through the study, according to an embodiment.

Disclosed herein is a method for comprehensive diagnosis and treatment monitoring of attention-deficit disorders, based, at least in part, on physiologically-measured parameters.

Attention deficit hyperactivity disorder (ADHD) is a neurodevelopmental disorder defined in DSM-V by inattention, hyperactivity, impulsivity, and characterized by the tendency to sustained inattention, distraction and suspension. Children and adolescents suffering from ADHD exhibit inability to screen out distracting stimuli and express impairments in academic achievement, behavioral aspect, emotional regulation and social functioning. Though ADHD prevalence estimation varies across countries and socio-demographic characteristics, the worldwide ADHD prevalence in children is 2%-7%, and it is approximated to reduce by half in adults.

The prevalence variability may stem from the variability in current diagnostic means, guidelines and different approaches. Primarily, ADHD diagnosis is based on an interview usually conducted by a physician according to the Diagnostic and Statistical Manual (DSM). Data is obtained from the subject and other sources (e.g., family members, teachers, etc.) and scored according to two categories: inattention and hyperactivity/impulsivity. ADHD evaluation of attention impairment as well as the response to medication might include computerized measures, most notably the continuous performance tests (CPT), such as the Test of Variables of Attention (TOVA). Particularly, these tests evaluate inattention while the subject is actively involved, and thus may suffer from low accuracy and sensitivity, which is their most important criticism. Moreover, these tests cannot evaluate the important dysregulation characteristic of ADHD.

Dysregulation in ADHD patients was previously suggested to affect a wide-range of everyday life functions, including sleep, appetite, sensory hyper or hypo-sensitivity, heart rate variability, and even the pitch of voice dysregulation. Measuring dysregulation in young childhood may act as a predictor of a full ADHD manifestation in adulthood, however, the TOVA measures (i.e. Response Time Variability) relate to the cognitive impairment component of attention deficit, rather than emotional dysregulation, and as such are not a particularly suitable test for this purpose.

Accordingly, in order to get a more integrative evaluation of the ADHD impact on the individual, there is a need to also measure the important dysregulation aspect in ADHD.

The Pre-Pulse Inhibition (PPI) paradigm is a direct and objective measure examining auditory sensory-motor functioning, aimed at depicting positive symptoms in schizophrenia. It represents an operational measure of information-protective toward pre-attentional mechanisms. Specifically, PPI is a neurological phenomenon in which a weaker acoustic pre-pulse inhibits the reaction to a subsequent strong startling pulse. The startle response brain circuitry undergoes preprocessing in the cochlear nuclei, up to the nucleus of the lateral lemniscus. Thereafter, it activates the motor center in the caudal pontine reticular nucleus, which sends descending projections to lower motor neurons of the limbs. Normally, when the pre-pulse appears just before the startling pulse, the attention system will detect it and inhibit the response to the startling pulse. The reduction of the response amplitude reflects the ability of the nervous system to temporarily adapt (and thus, regulate the response) to a strong sensory stimulus when a preceding weaker signal is given. The extent of response sustainment provides an indication to the extent of adaptation by the subject, wherein the subject recognizes that the pre-pulse predicts the appearance of the target stimulus, and thus does not react to the pre-pulse itself but rather suppresses the response until the target stimulus appears. The degree of adaptation by the subject may provide an indication of the level of dysregulation in the subject.

The beneficial effects of methylphenidate (MPH) treatment in ADHD were previously shown with respect to short term memory tasks, working memory tasks, inhibitory control tasks, Continuous Performance Tests, as well as in professional staff ratings. Recent studies have confirmed the efficacy and safety of MPH as the preferred first-choice medication for children and adolescents ADHD sufferers. However, although there is a clear evidence for the beneficial effects of MPH, there is still a controversy regarding the magnitude of the effect and the methods for estimating the effectiveness of MPH.

The current diagnosis of ADHD is mainly based on visual cognitive tasks, thus being exposed to motivational bias or differential diagnosis difficulties. In addition, though the importance of dysregulation in ADHD is emerging, it is still assessed by rating scales and during interviews, and not addressed by the common tests. Together, the latter may partially explain the fact that over the past decade, an increasing rate of children and adults diagnosed with ADHD and treated with stimulants such as Methylphenidate (MPH) has emerged, alongside reports on drug abuse. Though MPH has beneficial effects on ADHD symptoms and preschoolers' achievements, abuse of the drug may lead to long-term adverse consequences. Based on a rat model, it was previously found that MPH can lead to long term hormonal alterations related to hyper-anxiety and aggression (Avital, A., Dolev, T., Aga-Mizrachi, S., Zubedat, S., (2011). Environmental enrichment preceding early adulthood methylphenidate treatment leads to long term increase of corticosterone and testosterone in the rat. PLoS One 6, e22059). Moreover, in the case of a justified diagnosis of ADHD, the effectiveness of the drug type, dosage or dose and side effects should be individually evaluated and monitored to ensure optimal treatment parameters (i.e. maximal effectiveness with minimum side effects) and compliance (especially in young patients).

To date, continuous performance tests are still the leading decision-support neuropsychological assessment tools for ADHD screening, yet without the ability to detect attentional dysregulation nor distinguish or screen out external/internal co-factors such as caffeine intake, nicotine intake, dehydration, or emotional disorders such as anxiety disorders or even traumatic brain injury and schizophrenia. Although emotion dysregulation represents a major source of impairment in ADHD that reflects significant decline in peer relationships, family life, occupational attainment, and academic performance, it is crucial to distinguish it from attentional dysregulation, which may be detected using ASAT. While MPH is the efficiently leading treatment for ADHD, it is still not suitable for all cases of ADHD, regardless of the drug dose or pharmacokinetics.

Thus, it may be beneficial to separate the emotional component from any attentional dysregulation, for more efficient ADHD diagnosis and treatment. This is particularly beneficial when these two processes are suggested to overlap due to anomalies in orienting to emotional stimuli and recruiting the autonomic response.

Accordingly, in some embodiments, the present disclosure provides for a physiologically-measured ASAT-based protocol to detect a dysregulation aspect of ADHD, as part of an objective tool for a more comprehensive initial diagnosis and treatment monitoring. In some embodiments, the present disclosure further provides for an examination of the pre-post-treatment effects of MPH on the physiologically-measured auditory sustained attention, and as well as on the sympathetic nervous system activity of children suffering from ADHD.

In some embodiments, the present disclosure is based, at least in part, on physiologically-measured distinctive patterns of auditory sustained attention (ASAT) and dysregulation among ADHD patients, before and after MPH treatment, as well as EDA and startle response data which indicates that children suffering from ADHD produce higher startle probabilities and more electro dermal fluctuations. These measures are usually indicating hyper-arousal and high anxiety-related response. The baseline EDAs (both specific and non-specific) as well as the baseline eye blink probabilities to startle stimuli are higher in the ADHD group than in the controls. This may reflect the differences in dysregulation mechanism and anxiety, both being highly prevalent among ADHD patients. However, in some cases, these measures do not alternate following MPH treatment, wherein in a large sample meta-analysis of emotional dysregulation among ADHD groups, it was shown that ADHD had significant rates of emotion dysregulation compared to their counterparts controls, as indicated by elevation in measures of aggressive behavior in ADHD compared with non-ADHD populations. Furthermore, the startle response brain circuitry undergoes preprocessing in the cochlear nuclei, up to the nucleus of the lateral lemniscus. Thereafter, it activates the motor center in the caudal pontine reticular nucleus, which sends descending projections to lower motor neurons of the limbs. Evidently, this circuitry is not affected by MPH mechanism of action (i.e., blocking Dopamine and Norepinephrine reuptake), which is in accordance with reports on GABAergic neurons that govern the ventral nucleus of the lateral lemniscus.

In one embodiment, the present invention provides a method for assessing, determining or evaluating responsiveness of a subject to a treatment with an attention deficit hyperactivity disorder (ADHD) stimulant drug (also referred to as: stimulant ADHD drug). In one embodiment, the present invention provides a method for predicting responsiveness, effectiveness and/or safety of a treatment with an ADHD stimulant drug in a subject. In one embodiment, determining or evaluating responsiveness comprises assessing suitability, safety and/or efficacy. In one embodiment, determining or evaluating responsiveness comprises assessing the necessity. In one embodiment, determining responsiveness comprises assessing the necessity. In one embodiment, the present invention provides a method for determining whether an ADHD stimulant drug will be suitable. In one embodiment, the present invention provides a method for determining whether an ADHD stimulant drug will be suitable for treating a subject prior to prescribing or administering the ADHD stimulant drug to the subject.

In one embodiment, responsive comprises prone to be responsive or likely to be responsive.

In one embodiment, predicting comprises evaluating. In one embodiment, a method for predicting or evaluating comprises a method for evaluating or predicting the future effectiveness of a drug such as described herein in ameliorating, treating, and/or improving a disease or condition such as described herein. In one embodiment, a method for predicting or evaluating comprises a method for assessing the efficacy and/or responsiveness of a present treatment with a drug or a certain dosage or dose of a drug such as described herein. In one embodiment, insufficient ASAT and/or EDAs score of a subject according to the methods described herein requires treatment with a drug such as described herein, dosage or dose increase, or replacing the drug with a more effective drug.

In one embodiment, determining or evaluating responsiveness comprises predicting responsiveness, effectiveness, suitability, safety, efficacy or any combination thereof. In one embodiment, determining or evaluating responsiveness comprises predicting responsiveness, effectiveness, suitability, efficacy or any combination thereof of an ADHD stimulant drug or a given dosage or dose of an ADHD stimulant drug. In one embodiment, assessing suitability and/or efficacy comprises assessing the anticipated or expected suitability and/or efficacy. In one embodiment, determining responsiveness is determining the anticipated responsiveness. In one embodiment, determining responsiveness, efficacy, safety, suitability or any combination thereof according to the invention comprises conducting a non-specific electro-dermal responses (EDAs) analysis. In one embodiment, EDAs analysis is a predictive measure for the determining necessity of ADHD stimulant drug treatment or dosage or dose adjustment. In one embodiment, determining responsiveness, efficacy, safety, suitability or any combination thereof according to the invention comprises conducting an auditory sustained attention (ASAT). In one embodiment, ASAT analysis is a predictive measure for the determining necessity of ADHD stimulant drug treatment or dosage or dose adjustment. In one embodiment, conducting comprises preforming.

In one embodiment, the terms "dosage" and "dose" are used interchangeably. In one embodiment, the terms "dosage" or "dose" comprise the amount of drug administered. In one embodiment, the terms "dosage" or "dose" comprise the concentration of drug administered. In one embodiment, the terms "dosage" or "dose" comprise the amount of drug per kg body weight, administered. In one embodiment, the terms "dosage" or "dose" comprise blood concentration of a drug administered. In one embodiment, the terms "dosage" or "dose" comprise blood concentration of a drug administered over time or any pharmacokinetic value or combination of values.

In one embodiment, a subject as described herein is human. In one embodiment, a subject as described herein is a child. In one embodiment, a subject as described herein is diagnosed with a condition that may require treatment with an ADHD stimulant drug. In one embodiment, a subject as described herein is treated an ADHD stimulant drug. In one embodiment, a subject as described herein is in need of dosage or dose adjustment of ADHD stimulant drug. In one embodiment, a method as described herein provides data which enables determining the necessity for ADHD stimulant drug therapy. In one embodiment, a method as described herein provides data which enables dosage or dose adjustment (such as increase) of ADHD stimulant drug. In one embodiment, a method as described herein provides data which enables assessment of whether a given dosage or dose of an ADHD stimulant drug is sufficient or effective. In one embodiment, a method as described herein provides data which enables assessment of whether a given dosage or dose of an ADHD stimulant drug is insufficient and should be increased.

In one embodiment, a subject as described herein is afflicted with attention deficit hyperactivity disorder. In one embodiment, a subject as described herein is afflicted with a condition resulting in impaired alertness. In one embodiment, a subject as described herein suffers from at least one symptom associated with ADHD such as: inattention, hyperactivity, restlessness, disruptive behavior, and/or impulsivity.

In one embodiment, a subject in need of a stimulant ADHD drug has epilepsy. In one embodiment, a subject in need of a stimulant ADHD drug is afflicted with Tourette's syndrome. In one embodiment, a subject in need of a stimulant ADHD drug is afflicted with autism spectrum disorder. In one embodiment, a subject in need of a stimulant ADHD drug is afflicted with an anxiety disorder. In one embodiment, a subject in need of a stimulant ADHD drug is afflicted with intermittent explosive disorder. In one embodiment, a subject in need of a stimulant ADHD drug is afflicted with obsessive-compulsive disorder. In one embodiment, a subject in need of a stimulant ADHD drug is afflicted with reactive attachment disorder. In one embodiment, a subject in need of a stimulant ADHD drug is afflicted with a substance use disorder. In one embodiment, a subject in need of a stimulant ADHD drug is afflicted with oppositional defiant disorder. In one embodiment, a subject in need of a stimulant ADHD drug is afflicted with conduct disorder. In one embodiment, a subject in need of a stimulant ADHD drug is afflicted with primary disorder of vigilance. In one embodiment, a subject in need of a stimulant ADHD drug is afflicted with sluggish cognitive tempo. In one embodiment, a subject in need of a stimulant ADHD drug is afflicted with a mood disorder. In one embodiment, a subject in need of a stimulant ADHD drug is afflicted with restless legs syndrome.

In one embodiment, a method as described herein comprises the step of diagnosing or selecting a subject in need of a stimulant ADHD drug. In one embodiment, a method as described herein comprises the step of conducting a non-specific electro-dermal responses (EDAs) analysis on a subject. In one embodiment, a method as described herein comprises the step of administering a stimulant ADHD drug to a subject having higher value of EDAs compared to a control value. In one embodiment, a "control value" comprises a "control threshold value". In one embodiment, a method as described herein confirms and/or predicts responsiveness of a subject to a given dosage or dose of a stimulant ADHD drug. In one embodiment, a method as described herein assesses responsiveness, efficacy, safety, suitability or any combination thereof of a given dosage or dose of a stimulant ADHD drug in a subject treated with the given dosage or dose of the stimulant ADHD drug.

In one embodiment, a method as described herein is used for monitoring or continuously monitoring the effectiveness and safety of a stimulant ADHD drug in a subject treated with this stimulant ADHD drug. In one embodiment, a method as described herein is used for monitoring or continuously monitoring the effectiveness and safety of a certain dosage or dose of a stimulant ADHD drug in a subject treated with this certain dosage or dose of the stimulant ADHD drug. In one embodiment, a method as described herein is used for adjusting a dose of a stimulant ADHD drug, in a subject.

In one embodiment, control range or value (also referred to baseline) comprises a value or a range of a healthy subject. In one embodiment, control range or value (also referred to baseline) comprises a value or a range of a subject that is not afflicted with a disease or a condition such as described herein. In one embodiment, control range or value (also referred to baseline) comprises a value or a range of a subject that is not afflicted with: mental, developmental, neurological, behavioral, emotional, and/or attention related disease, disorder or deficit, disease and/or a condition such as described herein.

In one embodiment, control range or value (also referred to baseline) comprises a value or a range of a subject afflicted with a disorder, a disease or a condition such as described herein that is under the influence of an effective and safe dosage or dose of a drug such as described herein.

In one embodiment, a subject in need of an ADHD stimulant drug has a lower baseline ASAT performance across all pre-pulse intensities. In one embodiment, a subject in need of an ADHD stimulant drug has a lower baseline ASAT performance while this impairment is recovered following ADHD stimulant drug treatment. In one embodiment, a subject in need of an ADHD stimulant drug has a lower baseline ASAT performance while this impairment is recovered following an effective dosage or dose of an ADHD stimulant drug treatment.

In one embodiment, a method as described may partially be based on a positive correlation between ADHD stimulant drug dose and baseline or control non-specific EDA. In one embodiment, a method as described may partially be based on the distinctive patterns of ASAT and dysregulation among subjects in need of an ADHD stimulant drug, before and after ADHD stimulant drug treatment. In one embodiment, a method as described may partially be based on the EDA and startle response data which indicates that subjects in need of an ADHD stimulant drug produce higher startle probabilities and more electro dermal fluctuations. In one embodiment, a method as described may partially be based on an inverse relationship between baseline startle and EDA levels and ADHD stimulant drug treatment stability. In one embodiment, a method as described herein may partially be based on the ASAT finding that subjects in need of an ADHD stimulant drug therapy poorly responded to the pre-pulse stimuli, yet with a clear beneficial effect following ADHD stimulant drug treatment. In one embodiment, a method as described herein may partially be based on the finding that separating emotional from attentional dysregulation is essential for more efficient diagnosis and treatment of subjects in need of an ADHD stimulant drug.

In one embodiment, a subject having higher value of EDAs compared to a control value or range is responsive to a stimulant ADHD drug or to a dosage or dose of a stimulant ADHD drug. In one embodiment, a subject having lower baseline ASAT performance compared to a control value or range is responsive to a stimulant ADHD drug or to a dosage or dose of a stimulant ADHD drug. In one embodiment, a method as described herein comprises both steps of: an ASAT analysis and EDAs analysis. In one embodiment, a subject to be diagnosed with the need for treatment with a stimulant ADHD drug or dosage or dose adjustment (such as increase) of a stimulant ADHD drug has higher value of EDAs compared to a control, lower baseline ASAT performance compared to a control, or both.

In a recent study that examined the coherence of facial affect behavior and autonomic indices, using both the parasympathetic (respiratory sinus arrhythmia) and sympathetic (cardiac pre-ejection period) measures, it was found that parasympathetic functioning was diminished across both positive and negative induction conditions among children suffering from ADHD compared to their counterparts controls. Such evidence in abnormal imbalance of the autonomic nervous system activity among ADHD patients was also shown previously by others. For example, changes in ECG among non-treated ADHD were measured and compared to controls, where differences were found in the heart rate asymmetry analysis, such as orthostatic load associated with tachycardia. Similar alterations were also presented in baseline heart rate variability and galvanic skin response and demonstrated dysregulation in parasympathetic and sympathetic measures. Together, these reports support the findings underlying the present disclosure, which indicate inverse relationship between baseline startle and EDA levels and MPH treatment stability. Thus, it is suggested that there might be a preventive effect of MPH treatment, leading to better improvement in children that are stably treated with MPH, compared with those untreated.

Examining the auditory sustained attention test (ASAT) has revealed that children suffering from ADHD poorly respond to the pre-pulse stimuli, yet with a clear beneficial effect following MPH treatment. This beneficial effect of MPH is supported by previous reports on the positive effects of MPH on the sensory motor gating, and it may reflect a distinctive measure for attention dysregulation using ASAT, compared with the emotional dysregulation using EDA and startle reflex.

EXAMPLES

The present inventors have conducted a single-blind experiment (where a data manager is blinded to the group identification), parallel group RCT, one-center study. All subjects recruited from the Emek medical center, Afula, Israel.

A total of 351 children were screened, yielding eligible 189 children diagnosed with ADHD and 104 children without ADHD. Following enrollment, 47 children with ADHD and 41 age-matched controls were randomly assigned. FIG. 1 presents the CONSORT diagram of the flow of participants through the study.

Sample size was calculated to provide 85% statistical power. Children were diagnosed with an ADHD according to the DSM-V and scored for both inattention as well as for hyperactivity and impulsivity according diagnostic criteria. Eight children were excluded according to the exclusion criteria described below.

Screening criteria: (i) Subject aged between 7-18 years old; (ii) Meet the criteria of ADHD according DSM-V; (iii) Treated with Methylphenidate at a dose of 0.3-0.7 mg/kg; and (iv) Subject is treated with Methylphenidate for at least 2 months prior to the study.

Exclusion criteria: (i) Autism spectrum disorder; (ii) Chronic neurological disorders and chronic medical conditions (as diabetes) (iii) Schizophrenia spectrum and other psychotic disorders; (iv) Substance abuse (Drugs or Alcohol); (v) Depression; (vi) Hearing loss; (vi) Lack of cooperation; or (vii) Termination of participation due to personal decision.

This trial was registered in the National Library of Medicine (NLM) at the National Institutes of Health (NIH) trials registry system (# NCT02344784, https://clinicaltrials.gov/ct2/home).

The final experimental group included 39 ADHD children diagnosed with ADHD and treated with MPH and 37 age matched controls (demographic data is described in Table 1).

Cohort demographics included thirty-nine ADHD-diagnosed children with a mean age (10.87±2.83 SD), as compared to 37 age-matched controls (10.94±3.37 SD). Both groups represented unequal gender ratio of 82% boys among the ADHD group and 70% among the controls. In the ADHD group, 2 subjects suffered from tic disorder, while 11 subjects had a comorbidity of generalized anxiety disorder (F41.1) or anxiety disorder unspecified (F41.9). These children were included in the study since their treated comorbid disorder was stable. MPH treatment responsivity was also evaluated using a four-grades scale (e.g., "Bad," "Partial," "Good," and "Very good") and the current treatment stability in months (detailed in Table 1). Finally, 12 children had a history of second-generation DA-antagonist treatment, and 8 children had a history of antidepressant treatment.

Test subjects were escorted by their parents, and were asked not to take the MPH treatment in the morning of the experiment, and not to drink stimulating beverages such as coffee or energy drinks. The parents signed the consent form and provided the demographic data, following which the subject commenced the 3 steps procedure:

Baseline ASAT and EDA tests: The child was asked to sit on a stable chair in front of a computer screen, connected with EDA and EMG electrodes and requested to follow the instructions before wearing the headphones: "You will be hearing different types of tones, some will be powerful and some will be moderate. You do not have to do anything during this test, you only need to sit still and count how many tones you hear. When the session ends, all tones will be terminated"

Children diagnosed with ADHD were asked to take the MPH treatment and come back to the test room after 50 minutes. Controls were asked to take a break and return to the test room after 50 minutes.

Post 1-hour ASAT and EDA tests were conducted as at step 1.

Auditory Sustained Attention Test (ASAT)

A computerized human startle response monitoring system (SR-HLAB STARTLE REFLEX, San Diego Instruments, San Diego, CA) is used to deliver acoustic startle stimuli via headphones while recording the corresponding electro myographic activity from the orbicularis oculi muscle. Two disposable electrodes (sensor area 12 $mm^2$) are placed approximately 0.75-1 cm below the pupil on the orbicularis oculi muscle and 3rd reference electrode on the mastoid bone. The skin area at the electrode site is prepared using "skin prep" (3M, Red Dot, Cat. #2236).

The session starts with 3 minutes of acclimatization period with 57 dB background noise level that is delivered continuously throughout the session. The session is comprised from 68 pseudo-randomly delivered trails at 10 seconds average Inter-Trial-Interval (ITI, ranging from 6-14 seconds). Ten startle trials comprised of single 30 milliseconds of 108 dB "pulse alone" startle stimuli to evaluate the child startle magnitude and the probability to generate eye blink. Ten "No stimulus" trials were recorded in order to evaluate baseline noise levels. In order to evaluate pre-pulse inhibition (PPI), 40 "pre+pulse" trials consisted from a single 108 dB pulse preceded (100 milliseconds inter-stimulus-interval) by a 20 milliseconds pre-pulse of 6, 12, 18 or 24 dB above background noise (i.e. 63, 69, 75 or 81 dB), in addition to 8 "pre alone" stimuli trials (63, 69, 75 or 81 dB). The PPI is calculated as percent of the habituated/inhibited response as follows: 100−(max response to "pre+pulse" trial/max response to "pulse alone" trial×100).

Electro Dermal Activity (EDA)

Electrodermal activity was monitored by changes in the skin conductance. Two 5-mm-diameter Ag—AgCl electrodes (Mindlife, Jerusalem, Israel) were applied to the fingertips of the second and fourth digits of the non-dominant hand and secured with a Velcro band, as described previously. Electrodes were connected to a sensor and to an amplified receiver. An isolated skin conductance coupler (Mindlife) applied a constant 0.5V (DC) potential across the electrode pair and measured the conductivity at a sample rate of 10 Hz.

Different parts of skin may show different resistance change due to stress related sweating. In minimizing the variance that may arise due to this effect, it is suggested to record from the non-dominant hand of the subject.

Scoring of the EDA signal: During the 3 minutes acclimatization period (subjected only to a 57 dB background white noise), all electro-dermal responses were counted as non-specific EDAs. Following the first auditory stimulus and throughout the session, all electro-dermal responses were attributed as specific and event-related EDAs.

Statistical Analysis

Data was first screened for missing information, outliers and normality within variables using Kolmogorov-Smirnov and Shapiro-Wilk test. No missing data or extreme outliers were found. All variables were normally distributed among the controls, however, among the ADHD subjects only the ASAT didn't distributed normally.

Data was analyzed using a Two-way ANOVA for mixed design, with group as between-subject factor and test time as within-subject factor. Paired-as well as independent-samples t-test were used for post-hoc analysis. For the ANOVAS, effect size calculations were added (i.e., partial $\eta 2$). Associations between variables were calculated using linear regression or Spearman correlation when one of the variables is coded on ordinal scale. Analysis carried out by using IBM SPSS statistics software, and results were considered significant when the P-value was less than 0.05. Results are displayed as mean±S.E.M, unless otherwise specified.

Results—Auditory Sustained Attention Test (ASAT)

Figure 2B:
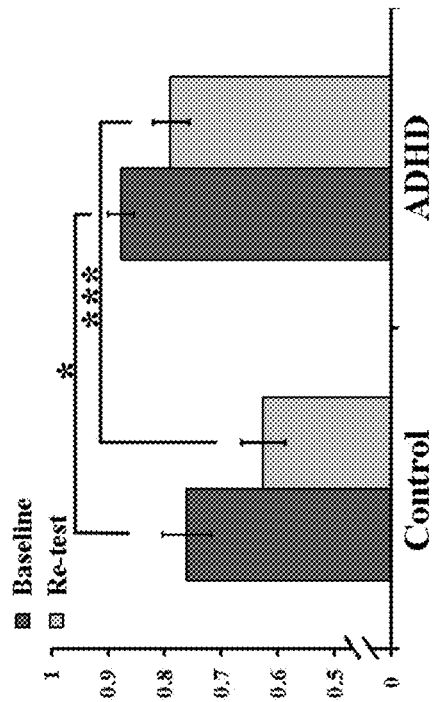
FIGS. 2A-2D show Auditory Sustained Attention Test (ASAT) test results in children.
Figure 2A:
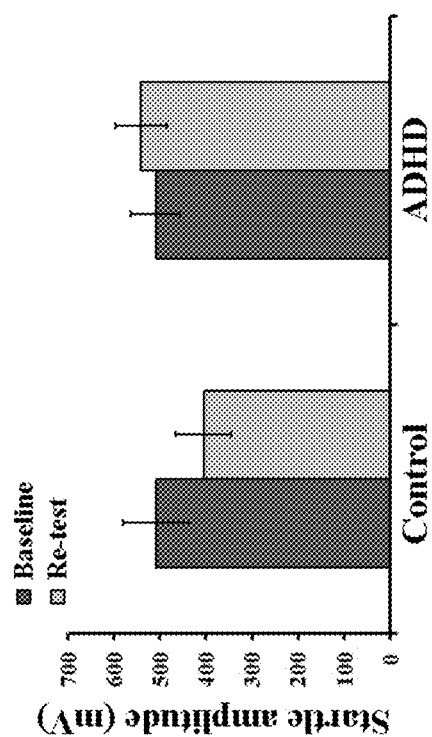
Figure 2D:
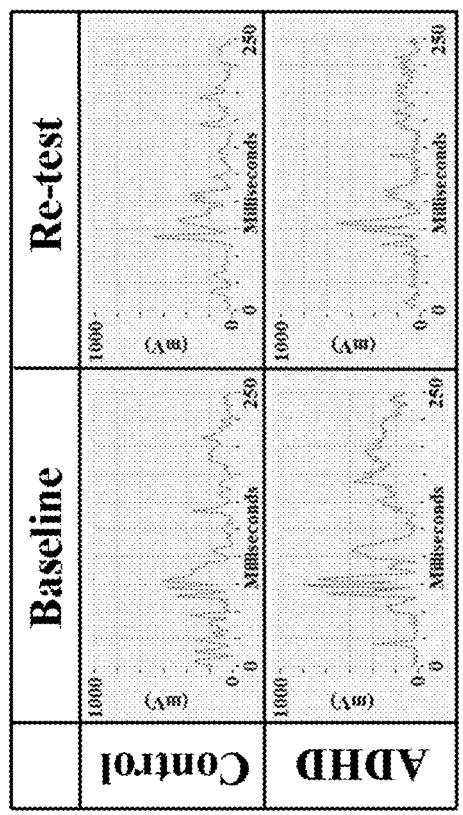

Two aspects of the startle response were measured—startle magnitude of the EMG signal (in millivolt) as well as the probability to generate an eye blink (0 or 1) regardless of amplitude values. No significant difference in startle amplitude was found (FIG. 2A) between groups ($F(1,74)=0.889$, $P>0.349$), test time ($F(1,74)=0.724$, $P>0.397$), nor the interaction group×test time ($F(1,74)=2.531$, $P>0.116$). However, measuring the probability of eye blinks following startle stimuli (FIG. 2B) revealed an elevated probability among the ADHD group ($F(1,74)=14.827$, $P<0.001$; $\eta 2=0.467$), and decreased probabilities at re-test ($F(1,74)=12.076$, $P<0.001$; $\eta 2=0.340$), with no significant interaction between group×test time ($F(1,74)=0.552$, $P>0.460$). Post-hoc t-test showed that compared with the controls, the ADHD group exhibited higher eye-blink probability to startle stimuli at both test ($P<0.019$) and re-test ($P<0.001$). Finally, both ADHD ($P<0.006$) and control ($P<0.025$) subjects decreased their startle probabilities at re-test.

Figure 2C:
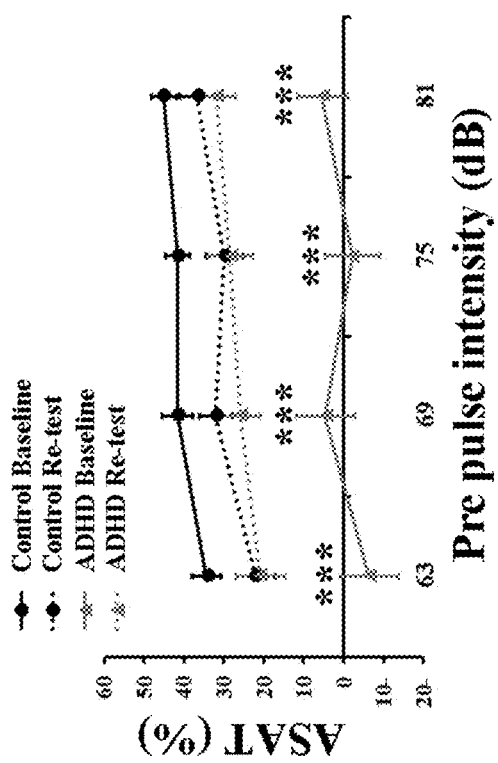

Analyzing the ASAT results, it was found a significant effect for group ($F(1,74)=23.291$, $P<0.0001$; $\eta 2=0.539$), test time ($F(1,74)=5.246$, $P<0.025$; $\eta 2=0.166$) as well as for the interaction group×test time ($F(1,74)=27.966$, $P<0.0001$; $\eta 2=0.474$). Post-hoc analysis revealed that children suffering from ADHD had lower baseline ASAT performance (FIG. 2C) across all pre-pulse intensities ($P<0.001$) while this impairment significantly recovered following MPH treatment.

Results—Electro Dermal Response (EDA)

Non-specific electro-dermal responses (EDAs) analysis (FIG. 3A) showed that the ADHD group exhibited higher values compared to the controls ($F(1,74)=23.791$, $P<0.0001$; $\eta 2=0.343$), and both groups showed decreased EDAs at re-test ($F(1,74)=9.846$, $P<0.002$; $\eta 2=0.317$) with no significant group×test time interaction ($F(1,74)=0.281$, $P>0.598$). Post-hoc analysis revealed that the ADHD group had significantly higher EDAs than controls, at both test ($P<0.001$) and re-test ($P<0.001$).

Figure 3B:
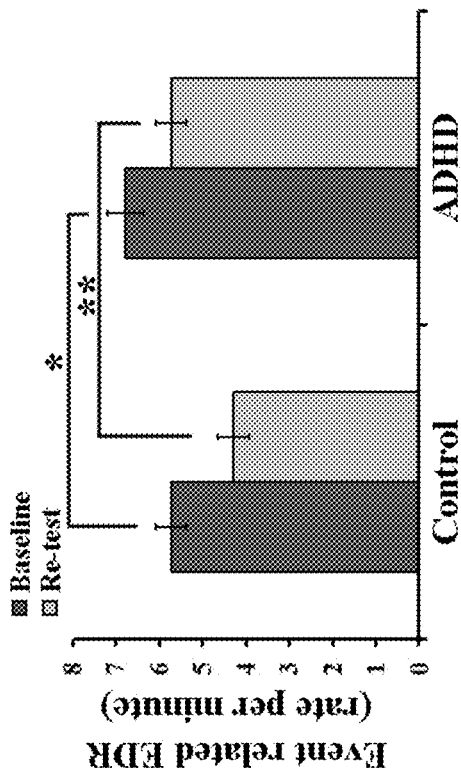
FIGS. 3A-3B Electro Dermal Activity (EDA) test results in children.
Figure 3A:
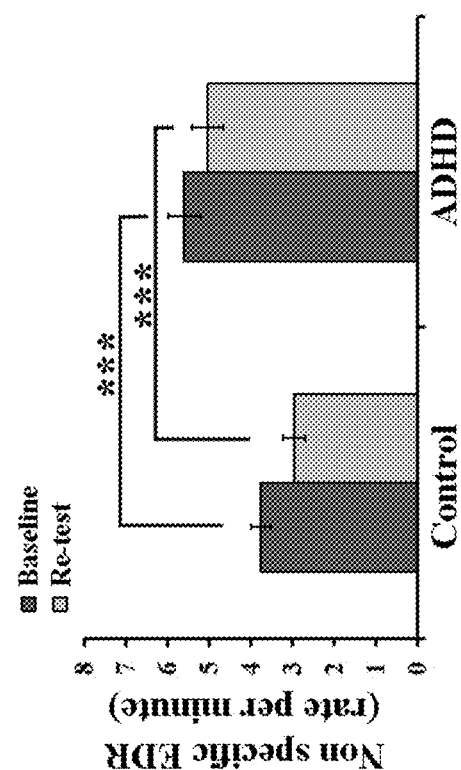

Similar pattern was observed for the event-related EDAs (FIG. 3B). The ADHD group exhibited higher event-related values compared to the controls ($F(1,74)=6.987$, $P<0.01$; $\eta 2=0.286$) and both groups showed decreased EDAs at re-test ($F(1,74)=31.143$, $P<0.0001$; $\eta 2=0.396$) with no significant group×test time interaction ($F(1,74)=0.760$, $P>0.386$). Post-hoc analysis showed that the ADHD group had significantly higher event-related EDAs compared to the controls, at both test ($P<0.05$) and re-test ($P<0.006$).

Demographics and Clinical Data

The mean age between ADHD and control groups did not differ significantly. Data regarding the DSM-V (Inattention and hyperactivity scores), treatment onset, dose or responsivity were collected only from ADHD patients.

Treatment onset (age when treatment initiated) was significantly and negatively correlated with total hyperactivity score ($Rp=-0.456$, $P<0.004$), total ADHD score ($Rp=-0.319$, $P<0.048$), as well as with MPH dose ($Rp=-0.299$, $P<0.032$) but not to any of the EDA or to the ASAT. This finding is not surprising as most of the children suffering from severe ADHD arrive earlier to the clinic and they tend to receive higher doses as a result of failed responsivity. The lack of correlation with the EDA and ASAT may also reflect a subjective bias of the physician in determining higher dose for severe ADHD.

Next, a positive correlation was found between MPH dose (mg/kg) and baseline non-specific EDA ($Rp=0.336$, $P<0.037$). However, analysis of covariance revealed that ADHD total symptoms severity ($t(38)=4.826$, $P<0.0001$) is a probable mediator between MPH dosage or dose and non-specific EDA's ($F(1,38)=2.302$, $P>0.138$).

Results—ASAT and EDA Predicting Treatment Responsivity

The four-graded scale of treatment responsivity is an ordinal scale measure, thus calculating Spearman's correlations, it was found that treatment responsivity is significantly and negatively correlated with baseline startle probabilities ($Rs=-0.294$, $P<0.035$) and marginally significant with baseline non-specific EDA ($Rs=-0.231$, $P>0.079$).

Treatment responsivity and stability (in months) were highly correlated ($Rs=0.893$, $P<0.0001$). I.e., good responsivity is correlated with long lasting treatment stability. Thus, treatment stability was further correlated with all dependent variables using forward hierarchical regression, aimed to explore possible predictors for treatment responsivity. It was found that both baseline startle probabilities ($Rp=-0.273$, $P<0.039$) as well as baseline non-specific EDA's ($Rp=-0.401$, $P<0.003$) contributed significantly to the model ($F(2,38)=7.558$, $P<0.002$) explaining 29.6% of the variance in treatment stability ($Rp=0.544$). While both startle and EDA did not inter-correlate, indicating a lack of multi-collinearity between these two measures, low values of eye blink probabilities as well as low non-specific EDA's at baseline negatively indicate treatment stability and responsivity.

Experimental Results—Medical Residents

The present inventors have conducted an experiment involving medical staff in the course of a residency at a medical facility. The objective was to asses examine the effects of extended shift duration on attention failures across several medical residencies. It is noted that tens of thousands of deaths occur due to medical errors each year, more than vehicle accidents, breast cancer and AIDS. Medical errors are assumed to be the 3rd leading cause of death in the US, but still, there is lack of public awareness and research around the topic. Thus, we aim to.

The study cohort included 109 residents sampled randomly from six different departments: Internal Medicine, Gynecology, Anesthesia, Surgery, Intensive Care Unit or Psychiatry.

Subjects were evaluated for attention parameters at baseline and post a 24-hour shift by measuring two distinct types of attention: covert novel physiological non-conceived attention (Auditory Sustained Attention Test, ASAT), and overt conceived attention (Test of Variable Attention; TOVA) and level of arousal (startle response). Data were collected anonymously.

Extended shift duration correlated with decreased alertness and dramatically impaired attention performance, with deficiencies below the normal range. We found approximately 40% overall attention impairment in the TOVA as well as a striking 70% impairment in the physiology measure ASAT. Attention impairment also differed between residents from each department, both at baseline and especially following a 24-hour shift: Psychiatrists may be viewed as having better attention skills, while ICU physicians have attention dysfunction as a group.

In this study, it was established that long shifts are strongly associated with attention failures. Our findings warrant consideration by international guidelines on residents' workload, especially in the context of residencies that are prone to preventable medical errors. also propose, for the first time, the ASAT as an objective physiological measure to indicate level of sensory dysregulation.

Physicians' work hours is a topic of a growing debate, recently culminating in national guidelines and legislation on duty hour restrictions 1, 2. In the United states (US), it has been reported that 44,000-98,000 deaths/year occur due to medical errors 3, the 3rd leading cause of death in the country, after heart disease and cancer. In Europe, medical errors occur in 8-12% of hospitalizations. Yet, medical errors are excluded from death certificates and national health statistics 4, 5. It was estimated that reducing the rate of medical errors would save 95,000 lives annually 4.

It was found that residents made substantially more serious medical errors under a frequent 24-hour shift schedule than when they worked under an intervention schedule with reduced work hours per week. It was found that residents working extended duration shifts had significantly more polysomnographically-recorded attentional failures during work hours, but the risk of adverse events (AEs) was not fully determined. In a large study of US residents, there was reported a positive association between extended duration shifts and medical errors, AEs, and attentional failures. The data relied on individual self-reports and was not independently validated. There is still a scarcity of research on residents' work schedules and preventable AEs during and after their shift.

Factors that alter cognitive function, attention and behavioral performance include sleep deprivation, fatigue, low alertness, and emotional dysregulation. The latter is defined as an individual's ability to modify an emotional state so as to promote adaptive behavior. Dysregulation arises when impairment is observed in adaptive processes that allow the individual to flexibly select, attend and appraise arousing stimuli, as commonly occurring during medical treatment. Moreover, a comprehensive review reported strong association between attention deficit and emotional dysregulation, to reach a ten-fold increase over population rates. Individuals with attention deficit and emotional dysregulation were significantly more impaired, compared with those with attention deficit alone, in various functions such as: peer relationships, family life, academic performance and occupational attainment. Together with other findings, an emphasize is emerging towards the need to directly and objectively measure attention impairment and its associated emotional dysregulation. Most of the scales for emotional dysregulation were not developed specifically for people with ADHD. Importantly, all the scale as summarized in a recent review, are either self-, parent-, teacher or clinician-report thus lacking objectivity and might suffer from limited sensitivity. Additionally, re-evaluation using the same subjective scale embedded the test-retest bias.

Sleep deprivation impairs the performance of both working memory and attention. Acute mental fatigue, induced by 90 minutes of a cognitively-demanding task, resulted in reduced sensorimotor functioning as measured by the Pre-Pulse Inhibition (PPI), a neurological sensorimotor reflexive phenomenon. It was recently suggested by that reflexive inhibition of response to a startling acoustic pulse following a pre-pulse (i.e., PPI), is modulated by attention functioning.

Here, it was investigated the impact of physicians' sleep deprivation due to workload on attention functioning in more than 100 residents. As a proof-of-concept, the aim was to examine the Auditory Sustained Attention Test (ASAT) as an objective physiological measure of attention and emotional dysregulation mechanisms 35, based on the PPI reflex in humans, and complement with the traditionally-used Test of Variables of Attention (TOVA).

Methods—Subjects

The study was conducted in the Emek Medical Center (Israel), and was approved by the local Institutional Review Board. Data were collected anonymously to increase compliance and to fulfill the IRB's requirements. The study included 109 residents sampled randomly and equally among males and females. Sample size was calculated to provide 90% statistical power. Participants belonged to the following medical departments: Internal Medicine, Gynecology, Anesthesia, Surgery, Intensive Care Unit (ICU) or Psychiatry.

Exclusion criteria: a diagnosed attention deficit disorder (e.g., ADHD) or sleep disorder, hearing deficit, active psychiatric or neurological disease, pregnancy, time spent within 1 month in a destination with over 2-hour (hr) time zone difference, regular use of sedative, stimulant, anxiolytic and/or antidepressant prescription. Diagnoses were based on self-reports.

Procedure

Residents were tested using ASAT and TOVA in a counterbalanced order. Measurements were taken in the morning for baseline and following a 24-hr extended duration shift. Caffeine and Nicotine were not allowed at least one hour before testing. Subjects reported normal sleep duration the night before the study as well as a normal shift workload. Consumption of caffeine and nicotine was monitored for in order to address possible confounding effects 37 (Table 1).

TABLE 1

Demographics, sleep duration, nicotine and caffeine intake.

| | Departments | | | | | | |
|---|---|---|---|---|---|---|---|
| | Internal (n = 31) | Gynecology (n = 16) | Anesthesia (n = 16) | Surgery (n = 16) | ICU (n = 16) | Psychiatry (n = 14) | Total (N = 109) |
| Age (years) | 32.54 (±6.44) | 33.85 (±3.23) | 39.71 (±7.54) | 35.25 (±4.78) | 41.4 (±9.71) | 33.66 (±6.20) | 34.52 (±6.91) |
| Relative percentage (%) | 28.44 | 14.67 | 14.67 | 14.67 | 14.67 | 12.84 | 100 |
| Rest duration (min) | 9.67 (±14.17) | 6.25 (±9.74) | 21.25* (±8.42) | 10.50 (±10.00) | 0 | 9.28 (±8.51) | 9.52 (±11.70) |
| Nicotine consumption (# Cigarettes) | 0 (6) | 0 (8) | 0 (6) | 0 (0) | 0 (4) | 0 (0) | 0 (8) |

TABLE 1-continued

Demographics, sleep duration, nicotine and caffeine intake.

| | Departments | | | | | | |
|---|---|---|---|---|---|---|---|
| | Internal (n = 31) | Gynecology (n = 16) | Anesthesia (n = 16) | Surgery (n = 16) | ICU (n = 16) | Psychiatry (n = 14) | Total (N = 109) |
| Caffeine consumption (cups number) | 5.93* (±4.01) | 4.56 (±2.50) | 3.12 (±1.99) | 2.93 (±1.34) | 5.81 (±4.23) | 0.78 (±1.25) | 4.20 (±3.46) |

From 3 pm until 8 am on the next day, residents were asked to record any significant resting periods (sitting or lying down).

TOVA:

V8.0 normalized by age and gender was used. In a 20-minute session, a flashing square is presented for 100 milliseconds (ms) with a 2 seconds (sec) inter-trial interval (ITI). Target and non-target stimuli are defined as the appearance of a small box on the top or bottom of the large square, respectively. Subjects press a micro-switch every time the target box appears and avoid pressing every time a non-target appears.

Parameters: omissions (OM): failing to click the micro-switch when the target was presented; commissions (CO): clicking the micro-switch when the non-target presented. Reaction time (RT): Time required to press the micro-switch after presented with the target. RT Variability (RTV): consistency level of response times. D-prime (D') ability to discriminate between target and non-target stimuli. Attention Comparison Score (ACS): overall attention performance. The set of raw scores was categorized using the following Standard Score (SS) data: SS>110 are above average, SS of 85-110 are average, SS 80-85 are considered borderline and SS<80 are not within normal limits. For ACS, score<0 was considered below the normal range. To minimize false-positives, overall performance was considered abnormal if three or more parameters were abnormal.

ASAT:

An automated human startle response monitoring system (SR-HLAB) was used to deliver acoustic startle stimuli and record electromyography activity. Two electrodes were placed below the pupil on the orbicularis oculi muscle and a 3rd reference electrode was placed on the mastoid bone.

Each session started with a 3-minute acclimatization period with 60 dB background noise level, delivered continuously throughout the session. Next, 28 trials were delivered and included eight randomly-delivered trials of single 40 ms 120 dB "pulse alone" startle stimuli to evaluate individual startle response (i.e., emotional arousal and dyregulation level), four "pre" stimuli trials (78 or 86 dB), and 16 "pre-pulse" trials that consist of a single 120 dB pulse preceded (120 ms inter-stimulus-interval) by a 20 ms pre-pulse of 18 or 26 dB above background noise (i.e. 78 or 86 dB). PPI was calculated as the percentage of response inhibition: 100−(max response to "pre-pulse" trial/max response to "pulse alone" trial×100) 31.

Statistical Analysis

Variables were first tested for normal distribution using skewness and kurtosis statistics. Two-way ANOVA for mixed design with departments as between-subject factor and test time as within-subject factor was performed. One-way ANOVA followed by Post-hoc Tukey tests were utilized to compare differences between departments. A paired sample t-test was used to compare baseline and post 24-hour shift performance. For all tests, effect size calculations were added (i.e. partial $\eta 2$ for ANOVA and Cohen's or Hedges' for two groups comparisons when the samples are equal or unequal, respectively).

Associations between variables were calculated using Pearson correlation coefficient. The statistical tests were conducted using Bonferroni adjusted alpha levels. Results were considered significant if P-value <0.05. Results are displayed as mean±S.E.M, unless otherwise specified.

Results

Demographics, Sleep Duration, Nicotine and Caffeine Intake:

Female residents rested longer than males (t(107)=2.070, P<0.041; Hedges' g=0.4) and males consumed more caffeine than females (t(107)=2.254, P<0.026; Hedges' g=0.422).

All residents had rested for no more than 45 minutes; rest time did not correlate with any of the examined attention variables. The Anesthesia residents rested for significantly longer time compared to all other residents (F(5,108)=7.216, P<0.001; $\eta$ 2=0.259).

Caffeine was tested for covariance and was found to have no effect over the attention variables. The Internal Medicine residents consumed most cups, while the Psychiatry residents consumed the least number of cups (F(5,108)=7.439, P<0.001; $\eta$ 2=0.265).

Cigarette smoking was not normally distributed; thus, this variable was described by median and range (Table 1).

Figures 4A, 4B:
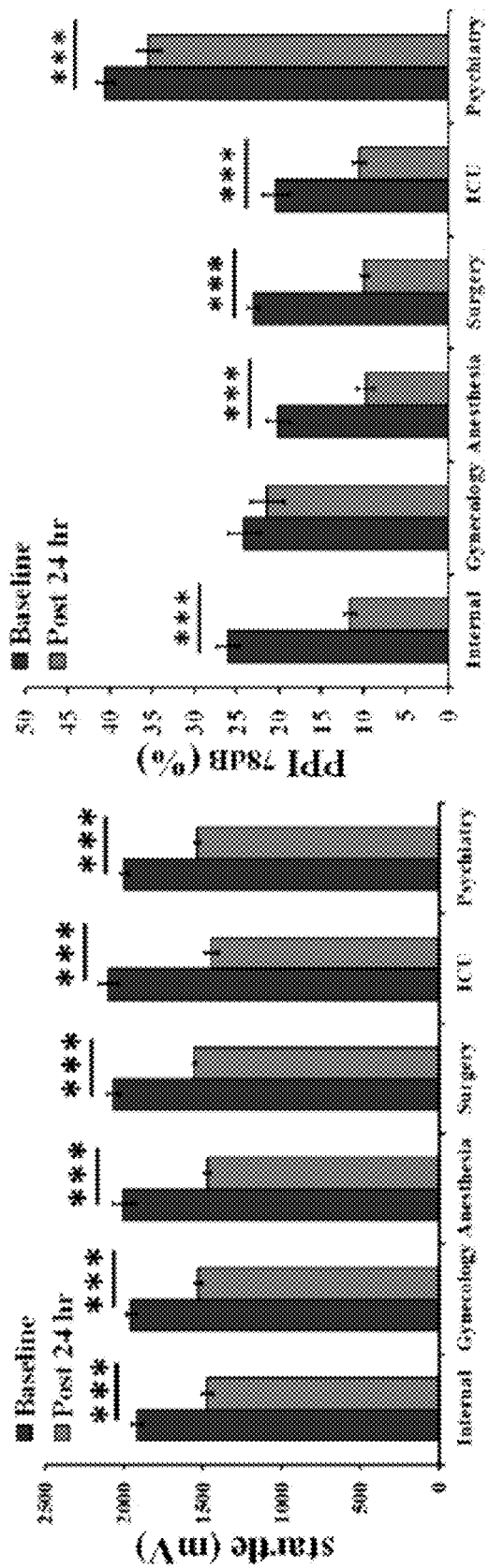
FIGS. 4A-4D show Auditory Sustained Attention Test (ASAT) test results in medical residents.

ASAT:

Startle response was significantly decreased following an extended shift among residents from all departments (F(1, 103)=426.167, P<0.001; $\eta$ 2=0.805) with no significant differences between them in a post-hoc analysis, nor a significant time×group interaction (F(5,103)=2.036, P>0.080; FIG. 4A).

Figure 4C:
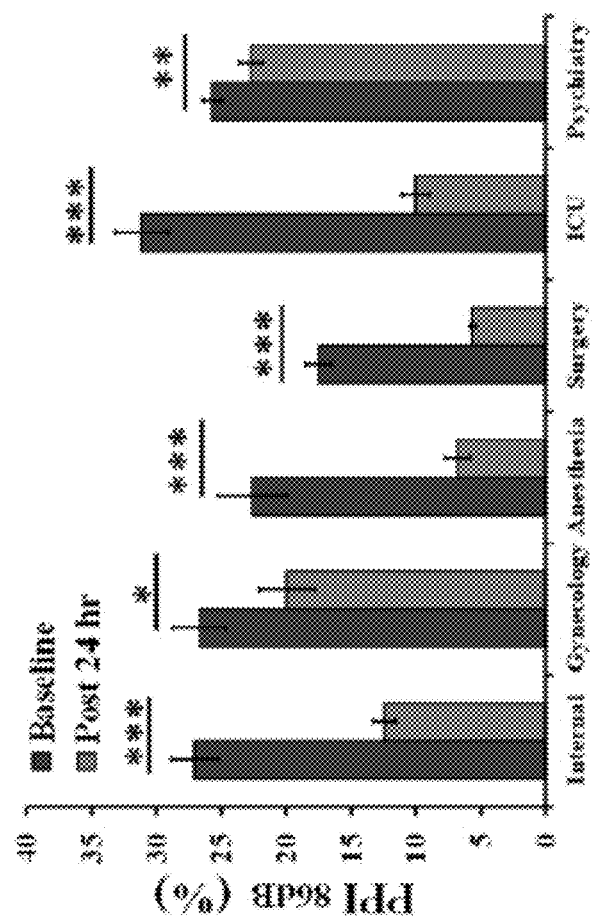
Figure 4D:
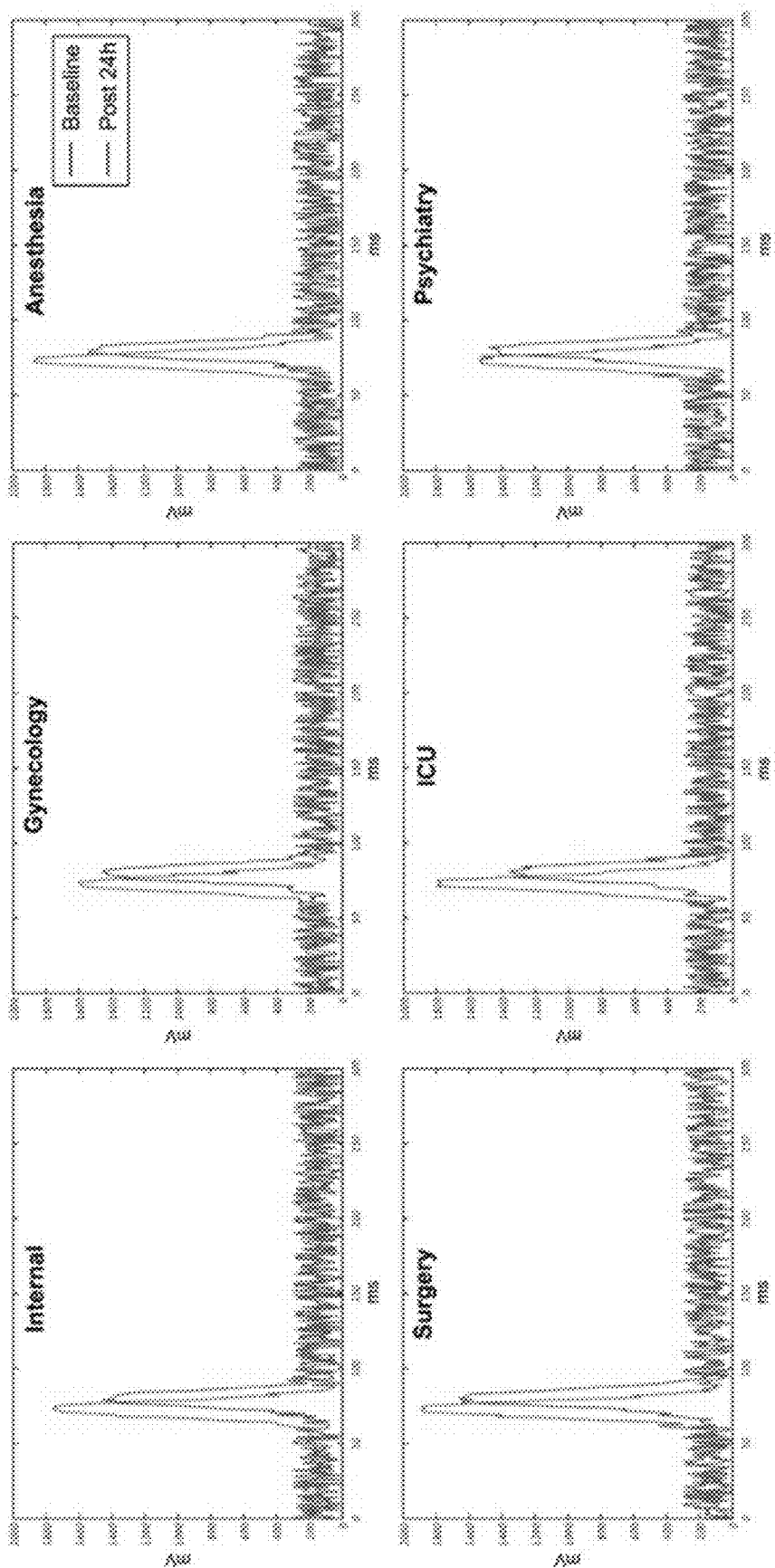
Figure 5A:
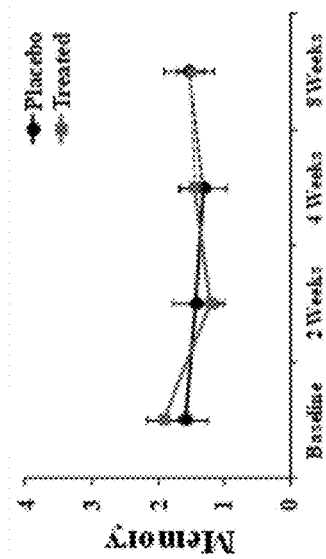
Figure 5B:
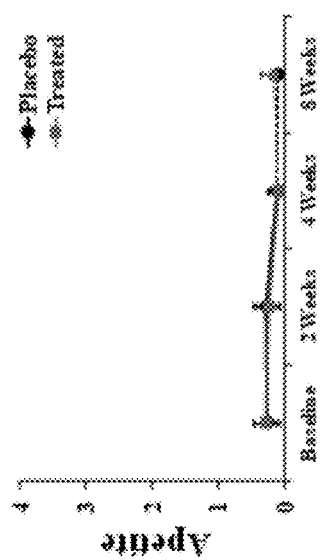
Figure 5C:
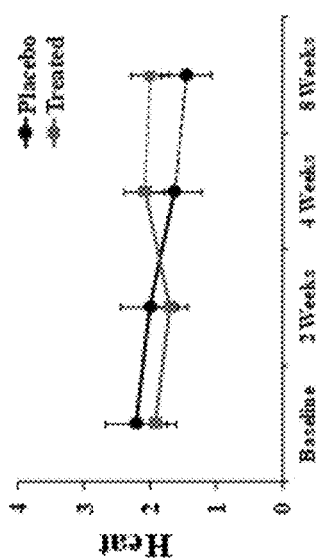
Figure 5D:
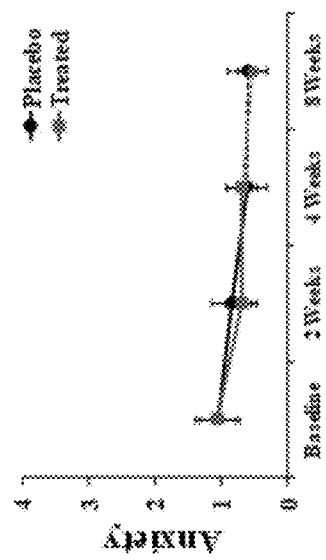
Figure 5E:
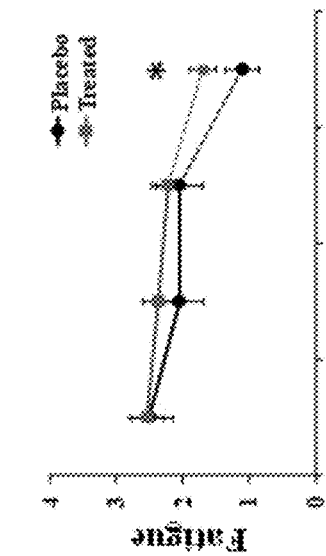
Figure 5F:
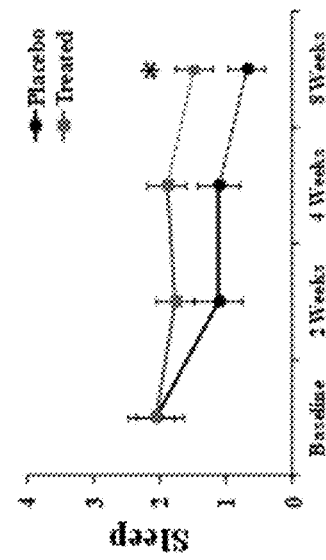

PPI:

performance was measured utilizing two distinct pre-intensities (78 dB or 86 dB) relative to the background noise, aimed to depict the dysregulation of signal-to-noise ratio. PPI results indicated a deteriorating attentional effect across all departments in both pre-intensities post-shift. However, Psychiatry and Gynecology residents were less affected, while others showed significant reduction in ASAT measure (FIG. 4B, 4Cc, 4D).

At 78 dB, it was found a main effect (F(1,103)=221.435, P<0.001; $\eta$ 2=0.750), a significant effect for department type (F(5,103)=61.953, P<0.001; $\eta$ 2=0.682) and a significant interaction between departments and test time (F(5,103) =9.762, P<0.001; $\eta$ 2=0.332). Extended shift reduced performance in all departments, however, Psychiatry residents still performed significantly better than all others (P<0.001) and had the highest inhibition ability at baseline (P<0.001).

At 86 dB, it was observed similar results, as Psychiatrists, once again, showed the best performance (P<0.001) followed by Gynecologists.

TOVA:

Results revealed deterioration across all parameters: ACS and OM declined from normal to abnormal SS; RTV and D' declined from normal to borderline SS (Table 2).

TABLE 2

Attention failures and level of impairment across parameters at baseline and post a 24 h shift.

| N = 109 | Parameter | | Baseline | Post-24 h | P-value/% change |
|---|---|---|---|---|---|
| TOVA (Standard Scores) | Omission rate | Attention Failure Average (±SD) | 85.53 (±20.30) | 78.88 (±20.06) | 0.0001 |
| | | % Impairment | 40.4 | 43.1 | ±2.7% |
| | Commission rate | Attention Failure Average (±SD) | 113.96 (±5.61) | 108.81 (±7.14) | 0.0001 |
| | | % Impairment | 0 | 1.8 | ±1.8% |
| | Mean reaction time | Attention Failure Average (±SD) | 115.62 (±6.06) | 113.53 (±7.09) | 0.0001 |
| | | % Impairment | 0 | 0 | 0 |
| | Mean reaction time variability | Attention Failure Average (±SD) | 101.44 (±14.68) | 89.59 (±13.48) | 0.0001 |
| | | % Impairment | 12.8 | 36.7 | ±23.9% |
| | D' | Attention Failure Average (±SD) | 99.25 (±15.26) | 89.19 (±15.51) | 0.0001 |
| | | % Impairment | 17.4 | 32.1 | ±14.7% |
| | ACS | Attention Failure Average (±SD) | 0.82 (±2.96) | −1.35 (±2.74) | 0.0001 |
| | | % Impairment | 27.5 | 68.8 | ±41.3% |
| ASAT | Startle (mV) | Attention Failure Average (±SD) | 1994.62 (±191.99) | 1496.94 (±138.07) | 0.0001 |
| | | % Impairment | N/A | N/A | N/A |
| | PPI 78 dB (%) | Attention Failure Average (±SD) | 25.51 (±8.55) | 15.44 (±9.66) | 0.0001 |
| | PPI 86 dB (%) | Attention Failure Average (±SD) | 25.39 (±8.92) | 12.68 (±7.47) | 0.0001 |
| | PPI total | % Impairment | 6.42 | 77.06 | ±70.64% |

Hence, the decline was not merely statistical but clinical, from a normal to an abnormal spectrum. Surprisingly, eight (7.3%) physicians were found to have abnormal baseline performance in at least three parameters. Since ADHD diagnosis cannot be made solely based on TOVA, these subjects are referred to as the 'ADHD-like group'. TOVA parameters are summarized in Table 3.

TABLE 3

| | TOVA parameters across departments. | | | | | | |
|---|---|---|---|---|---|---|---|
| | Parameters | Internal (n = 31) | Gynecology (n = 16) | Anesthesia (n = 16) | Surgery (n = 16) | ICU (n = 16) | Psychiatry (n = 14) |
| Baseline | Omission rate | 90.61 (±19.92) | 89.63 (±17.71) | 84.56 (±19.93) | 81.63 (±14.15) | 63.06 (±20.37) | 100.86 (±0.36) |
| | Commission rate | 115.19 (±5.75) | 113 (±4.23) | 110.63 (±5.66) | 115.06 (±3.49) | 109.5 (±4.59) | 120 (±2.39) |
| | Mean reaction time | 115 (±5.96) | 117.13 (±3.85) | 119.38 (±5.54) | 113.44 (±3.78) | 111.69 (±7.67) | 118.43 (±5.61) |

TABLE 3-continued

TOVA parameters across departments.

| | Parameters | Internal (n = 31) | Gynecology (n = 16) | Anesthesia (n = 16) | Surgery (n = 16) | ICU (n = 16) | Psychiatry (n = 14) |
|---|---|---|---|---|---|---|---|
| | Mean reaction time variability | 96.03 (±16.7) | 97.94 (±9.81) | 94.94 (±9.11) | 116.56 (±14.01) | 97.81 (±10.34) | 111.71 (±6.43) |
| | D' | 100.74 (±16.85) | 98.13 (±17.39) | 101.88 (±3.54) | 98.69 (11.65) | 84.75 (±15.19) | 111.43 (±7.64) |
| | ACS | 0.71 (±3.07) | 0.54 (±2.41) | 0.85 (±1.10) | 1.67 (±1.81) | −1.68 (±4.43) | 3.25 (±1.10) |
| Post 24 h | Omission rate | 78.06**** (±20.51) | 82.94*** (±16.18) | 77.13**** (±19.29) | 69.63* (±19.33) | 72.31 (±24.68) | 96.14**** (±1.35) |
| | Commission rate | 110.48**** (±7.56) | 108.19**** (±4.89) | 102.44**** (±8.31) | 111**** (±3.37) | 105.81* (±7.08) | 114**** (±3.28) |
| | Mean reaction time | 112.13* (±7.19) | 114.38**** (±3.85) | 116.5**** (±5.18) | 110.38* (±5.25) | 109 (±8.64) | 121.07 (±4.10) |
| | Mean reaction time variability | 64.32**** (±16.01) | 85.5**** (±11.62) | 82.56**** (±11.24) | 96.5**** (±6.82) | 90.81**** (±7.08) | 104.64** (±7.24) |
| | D' | 84.42**** (±18.26) | 91**** (±15.78) | 89.69**** (±6.59) | 86.19** (±13.27) | 86.19 (±17.23) | 104**** (±5.33) |
| | ACS | −2.04**** (±2.81) | −1.75**** (±2.77) | −1.38**** (±1.18) | −1.81**** (±1.96) | −2.09 (±3.46) | 2.07** (±0.88) |

Omission:

SS (OM-SS) significantly decreased across residents from all departments post-shift and differed between departments ($F(1,103)=18.300$, $P<0.001$; $\eta 2=0.217$), excluding the ICU residents that already presented abnormal impairment at baseline. There was also a significant interaction of department and test time ($F(5,103)=6.269$, $P<0.001$; $\eta 2=0.233$).

Commission SS (CO-SS) significantly declined ($F(1,103)=211.363$, $P<0.001$; $\eta 2=0.672$) and differed between residents from each department ($F(5,103)=8.232$, $P<0.001$; $\eta 2=0.286$), with a significant interaction found between department and test time ($F(5,103)=3.304$, $P<0.001$; $\eta 2=0.138$). Post-hoc paired sampled analysis revealed impairment among residents from all departments post-shift. Psychiatry residents had the highest baseline CO-SS as well as the lowest decline rate, meaning better CO-SS. Anesthesia residents had the greatest decline rate reaching the lowest SS.

Reaction Time:

SS (RT-SS) was within the normal range at baseline in residents from all departments and deteriorated in some departments following shift ($F(1,103)=18.429$, $P<0.001$; $\eta 2=0.152$). RT-SS significantly differed between residents ($F(5,103)=6.806$, $P<0.001$; $\eta 2=0.248$), and an interaction was found for department and test time ($F(5,103)=3.625$, $P<0.005$; $\eta 2=0.150$). At baseline, the Psychiatry residents exhibited high RT-SS and displayed a significantly shorter RT post-shift than all other departments. Post-hoc paired analysis revealed impairment in all but Psychiatry and ICU residents.

RT Variability:

SS (RTV-SS) was within the normal range among residents from all departments at baseline and significantly higher after 24 hours ($F(1,103)=208.528$, $P<0.001$; $\eta 2=0.669$). RTV-SS differed between residents ($F(5,103)=9.451$, $P<0.001$; $\eta 2=0.314$), and department and test time significantly interacted ($F(5,103)=5.276$, $P<0.001$; $\eta 2=0.204$). Post-hoc paired sample analysis revealed a significant impairment among residents from all departments. However, post 24-hr, Surgery, ICU and Psychiatry residents scored within the normal range/value compared to Internal Medicine ($P<0.011$) and Anesthesia ($P<0.015$), which scored at an abnormal level. This exemplifies that not all observed deteriorations were clinically-significant since some scores remained only borderline-abnormal or within the normal range post-shift.

D Prime:

SS (D'-SS) decreased significantly among in all residents except the ICU residents post 24-hr shift ($F(1,103)=50.5$, $P<0.001$; $\eta 2=0.329$) and decreased differently in the various departments ($F(5,103)=4.945$, $P<0.001$; $\eta 2=0.194$). A significant interaction between test time and department type was also found ($F(5,103)=4.552$, $P<0.001$; $\eta 2=0.181$). ICU residents had the lowest baseline D'-SS but within the normal range/value. Post-shift, Psychiatrists showed the highest D'-SS values. Post-hoc paired sample analysis discovered significant impairment in all but the ICU residents.

ACS:

decreased significantly following shift ($F(1,103)=127.803$, $P<0.001$; $\eta 2=0.554$), and differed between the residents ($F(5,103)=5.844$, $P<0.001$; $\eta 2=0.221$); with a significant interaction between test time and department type ($F(5,103)=6.043$, $P<0.001$; $\eta 2=0.227$). ICU residents had the lowest score at baseline and below the normal range/value and Psychiatry residents had the highest baseline score. Post-shift, the Psychiatrists still showed the highest ACS compared to residents from other departments ($P<0.001$) and were the only residents from remaining within the normal range/value. Post-hoc paired sample analysis revealed a significant post-shift impairment among all residents, excluding the ICU residents, which remained abnormal from baseline.

ASAT and TOVA Overall Impairment and Correlations

Extended shift significantly impaired all TOVA and ASAT parameters ($P<0.001$), as demonstrated by the increasing percentage of ADHD-like subjects in all parameters but RT-SS post-shift. Inter-residential performance deteriorated from normal baseline values to abnormal OM-SS and ACS (Tables 2 and 4).

TABLE 4

TOVA and ASAT correlations coefficients at baseline and post-24 h shift.

| PPI | Omissions | Commissions | Reaction time | Reaction time variability | D' | ACS |
|---|---|---|---|---|---|---|
| Baseline | 0.308** | 0.252** | 0.153 | 0.063 | 0.224* | 0.218* |
| Post 24 h | 0.385** | 0.251** | 0.356** | 0.315** | 0.376** | 0.402** |

ASAT and TOVA parameters correlated at baseline and to a greater extent post-shift. At baseline, PPI showed significant and weak correlation with OM-SS (r=0.308, P<0.01), followed by CO-SS (r=0.252, P<0.01), D'-SS (r=0.224, P<0.05) and ACS (r=0.218, P<0.05). Post-shift, PPI also correlated with RT-SS and RTV-SS and had a moderate correlation (P<0.01) with ACS (r=0.402), OM-SS (r=0.385), D'-SS (r=0.376), RT-SS (r=0.356), RTV-SS(r=0.315) and CO-SS (r=0.251) (Table 4).

The ADHD-Like Group

A small group of eight residents (7.34%) shared decreased performance at baseline (SS<1.5 standard deviations below average in at least three parameters). The group had abnormal baseline values in OM-SS, D'-SS and ACS and included two ICU, one Surgery and five Internal Medicine residents. Interestingly, those residents were less affected by the lack of sleep compared to Gynecologists and residents from Anesthesia department that scored at baseline within the normal range/value, and showed a deteriorating performance only in the RTV parameter that is considered the most sensitive for attention deficit 38 (supplementary Tables 1 and 2).

Discussion

Using ASAT as a novel physiological measure of attention yielded a sensitive indication for the effect of extended shift on attentional failure, across residency types. Specifically, a 24-hr shift was associated with both covert and overt attention failures, suggesting that residents were negatively affected by work schedule in both arousal level and attention.

Previous studies showed deterioration in psychomotor vigilance performance tasks 39 and in recall memory and concentration 40 after extended duration shifts. In contrast, residents made significantly less momentous errors during a pilot intervention schedule that eliminated extended work shifts 6. In the ASAT assessment, a similar effect of decreased arousal level across residents from all departments was probably due to low alertness, reflecting emotional dysregulation. The effect of partial sleep deprivation can be counted as an additional wakefulness state that has a neurobiological cost which accumulates over time 41.

Mechanistically, it has been shown that affectively charged negative stimuli receive enhanced early sensory encoding in adults with attention deficit 42, 43. This 'bottom-up' effect was reduced when the stimuli were positive, thus, supporting our hypothesis that startle stimuli cause over-perception. Indeed, Conzelmann et al. 44 showed abnormal early processing of emotional stimuli in attention deficit. Similarly, this was evident in our results as a consistent reduction of startle response observed in all subjects, accompanying the decrease in ASAT assessment, following extended shift.

Moreover, it was previously reported that while in typically developing children the autonomic nervous system function tracks the valence of emotional stimuli (prominently for negative stimuli), in children with ADHD this 'top-down' regulation is partially lost 45.

Considering the inherent role of startle stimuli in the measurement of ASAT (using various pre-pulses), it may be attributed to physiologically measure both attention attenuation together with emotional dysregulation.

Our postulation harks back to early conceptualization, positing emotional dysregulation as a core symptom in ADHD together with hyperactivity, impulsivity and inattention, also for state-dependent attention deficit.

Using TOVA, the impact of extended shift was most pronounced in the ACS, followed by RTV-SS and D'-SS. Notably, borderline OM-SS at baseline trended toward abnormal values post extended shift. This deterioration carries clinical implications as it was observed in all parameters, excluding RT-SS and CO-SS; the latter indicates a preserved inhibition control among physicians.

The observation that at baseline the departments differed in attention but not in arousal elucidates the underlying attention mechanism and demonstrates the specificity of the ASAT as a novel diagnostic tool. Based on the attentional difference between residents, it may be hypothesized that functional capabilities may affect the choice of residency. For example, Psychiatrists may be viewed as having better attention skills, while ICU physicians have attention dysfunction as a group.

ASAT measurement was found to be most sensitive to 24-hr shifts. Thus, based on the ASAT, Gynecologists and Psychiatrists demonstrated the least impact on covert non-conceived attention ability, while Anesthesia and ICU residents suffered the most significant deterioration post 24-hr shifts.

Significant attention impairments in TOVA parameters were detected among all residents. Psychiatrists had the best baseline scores and remained within the normal range post-shift, while residents from other departments showed pathological impairment post-shift in at least one parameter; indicating clinical differences. Interestingly, ICU residents did not decrease their OM-SS, D'-SS and ACS score post-shift, which were already borderline-abnormal at baseline. Further research is needed to elucidate whether the negative effect of shift duration on attention lessens if/when the baseline attention impairment is more severe.

Post-shift, residents of most departments tended to behave as suffering from "ADHD predominantly inattentive". Accordingly, the expected impaired executive functions were attention and processing speed, but not inhibition. Clinically, it could mean that these residents are not more impulsive at the end of their shift but might be slower and less attentive (decrease in span and accuracy), which could lead to grave, but preventable medical oversights.

Surprisingly, at baseline 7.34% of residents from the ICU, Surgery and Internal departments had abnormal levels of performance, which may indicate an undiagnosed, self-unaware attention deficit disorder. The fact that all physicians had normal inhibition control may explain why none of the participants reported any dysfunction at study entry.

Extended shift duration had no impact on the "ADHD-like" group. A possible explanation is that ADHD-prone persons may be less susceptible to the negative effect of extended shift duration due to the exacerbation of sleep disorders associated with ADHD 46. If so, the results demonstrate the diminished effect of external sleep disorder given a prior attention deficit disorder.

Compared with TOVA, the ASAT is a new tool for evaluating attention 31. The association between the tests were more pronounced post-shift, when the subjects performed in an ADHD-like manner.

ADHD is associated with dysregulation of multiple systems, including sleep, appetite and sensory perception, thus, the ASAT importance stems from the ability to test the availability of sensorimotor regulating mechanisms as they rely on a much higher velocity response (40-60 ms) compared to the TOVA reaction time (>200 ms) that measures prefrontal executive functions. Thus, the two tests complement one another and may allow to collectively address ADHD, executive dysfunction and dysregulation, which are usually addressed separately.

Accordingly, dramatic attention failures were recorded and emotional dysregulation among residents scheduled to work long hours. Our results sub-serve as proof-of-concept for the use of the ASAT as novel, noninvasive physiological measure of both attention attenuation and emotional dysregulation. Practically, the results emphasize the need for intervention programs and improved regulations to cope with the emotional dysregulation and attentional failure's possible consequences, such as medical errors and associated hazards 47. Pending more research, our findings also support factoring in residency type in future guidelines (e.g., shorter shifts for ICU residents). Shift duration decisions should rely on periodical attention monitoring, to verify low risk for medical error.

Experimental Results—Breast Cancer Patients

A study included 38 treated females (Mean age=47.50, Sd=10.06) compared to 19 females treated with placebo (Mean age=43.63, Sd=11.88) with no significant differences. Body mass index was also not statistically different among treated group (Mean=26.14, Sd=6.84) compared to placebo (Mean=24.76, Sd=4.14). Finally, tumor size of both treated group (Mean=3.20, Sd=1.72) as well as placebo (Mean=3.13, Sd=1.86) was not statistically different. Finally, the ratios between both groups in all independent parameters measured in table 1 below were evaluated. In short, it was found significant differences in the ratio for estrogen receptor test between treated group and placebo. In addition, there was found significant differences in the ratio of antidepressants treatment between both groups.

Effect of Homeopathic Treatment on Fatigue and Attention

Clinical interview revealed no significant differences in anxiety, memory impairments, appetite nor in hormonal heat waves. However, there was found significant effect for homeopathic treatment at fatigue levels ($P<0.023$; FIG. 5, panel C) and sleep disorders ($P<0.05$, FIG. 5, panel E) at 8 weeks test (4 weeks post last treatment) displayed in FIG. 5.

Figures 6A, 6B:
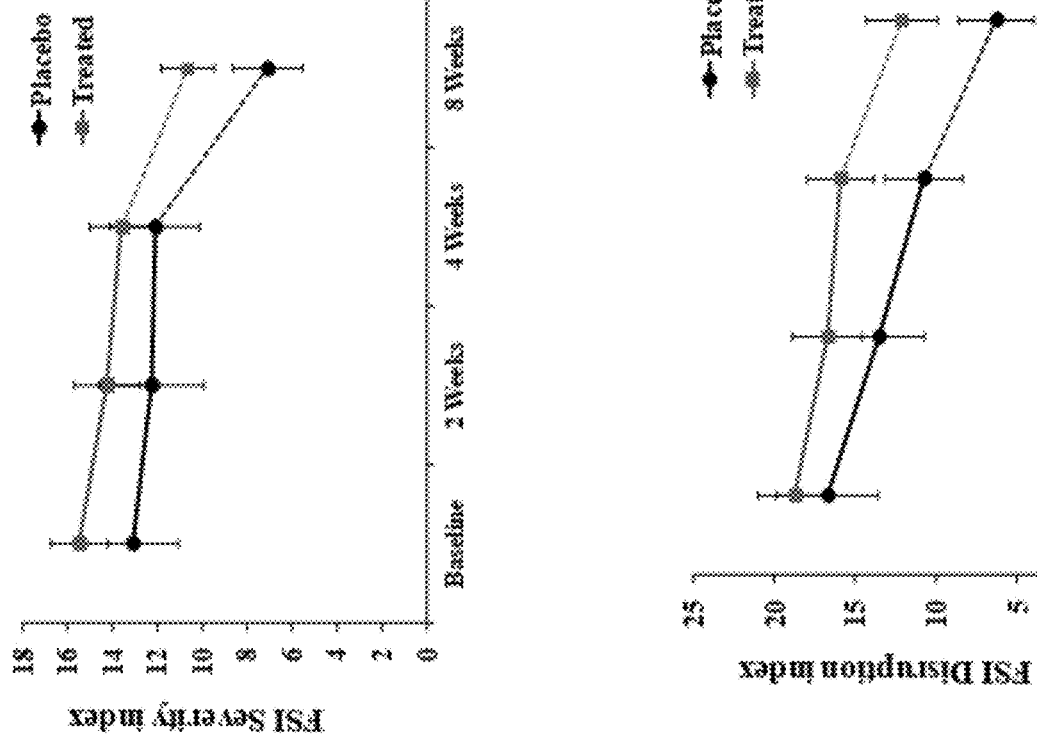

Measuring the fatigue levels using the fatigue symptom inventory (FSI) questionnaire (FIG. 6, panels A, B), there was found a that treated group tended to feel more tired starting from the baseline tests while both groups had lower fatigue levels during the radiation session and continued through the recovery period (4 weeks after the last radiation treatment), however, there was found no significant differences between groups.

Figures 7A, 7B, 7C:
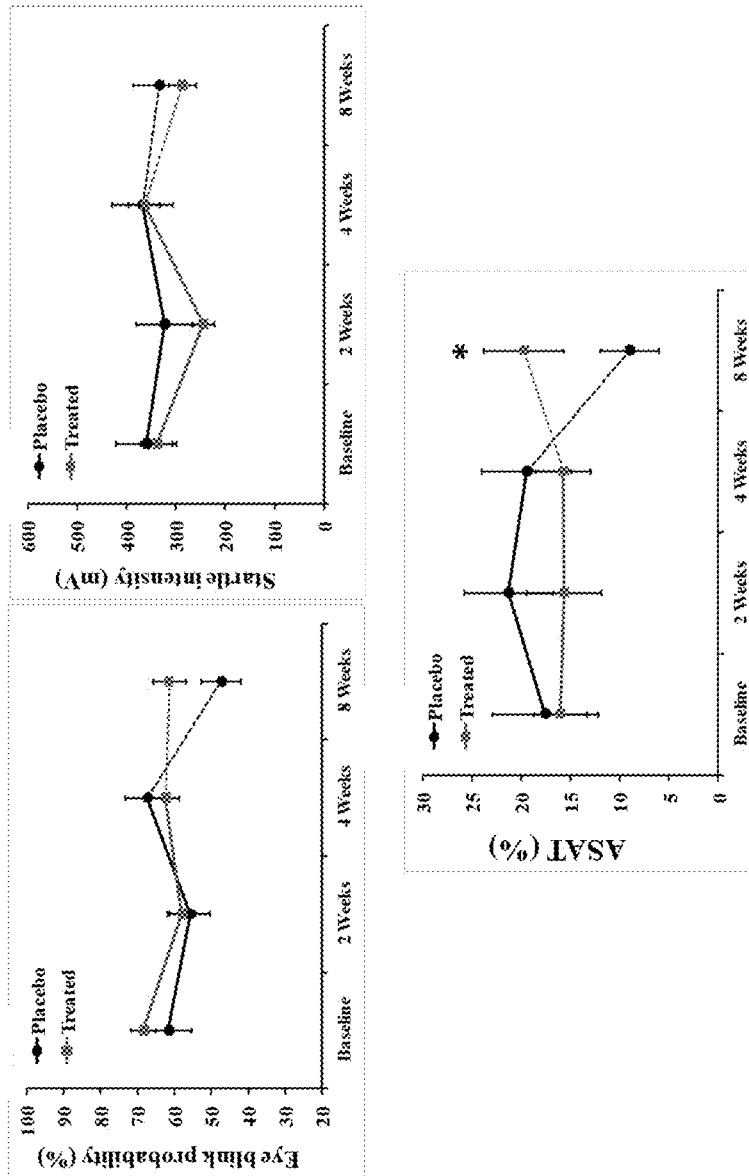
Figure 8A:
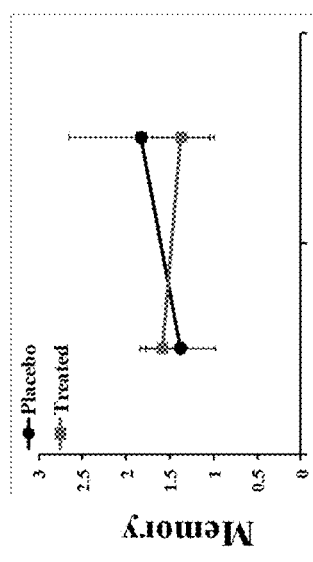
Figure 8C:
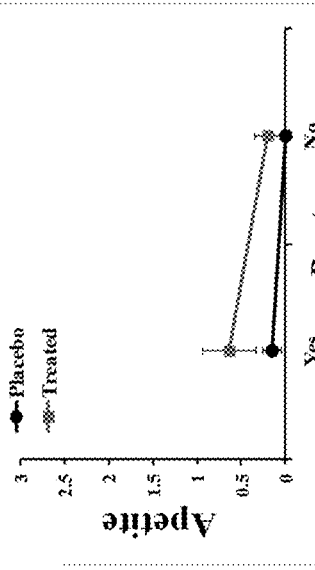
Figure 8E:
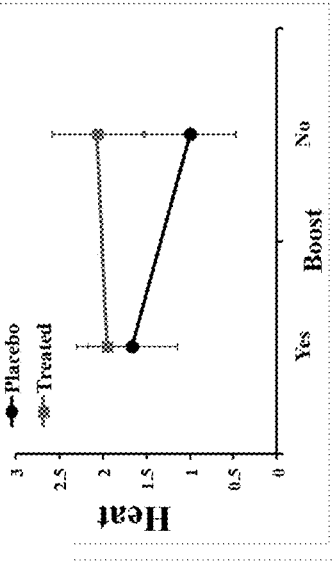
Figure 8B:
Figure 8D:
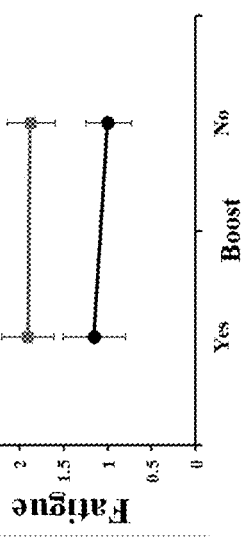
Figure 8F:
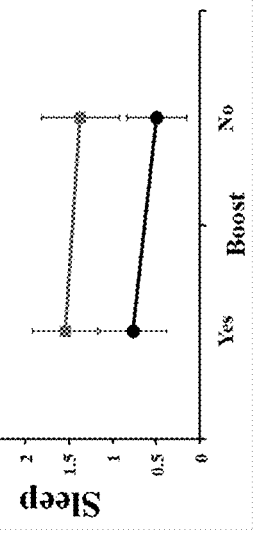

In order to evaluate the differences in anxiety (startle response) as well as attention (ASAT) following homeopathic treatment, ANOVA was performed for mixed design and found a general reduction in anxiety (FIG. 7, panels A, B) among both group (treated and non treated) $F(3,147)=4.240$, $P<0.007$), with no significant differences between group. However, when measuring the attention ability, there was found that treated group displayed significant improvement in ASAT ($P<0.035$, FIG. 7, panel C) compared to placebo group 4 weeks post the last radiation therapy (at 8 weeks).

Effect of Chemotherapy on Fatigue and Attention
Effect of Boost on Fatigue and Attention Following the main effects received at the last recovery point, the main effects were evaluated using 2 way ANOVA for mixed design for both boost of radiation therapy as well the homeopathic treatment in order to see whether these effects are dependent (FIG. 8, panels A-F). It was found that both fatigue and sleep deprivation found previously are similar for both with or without radiation boost (FIG. 8, panels C, E).

Figures 9A, 9B:
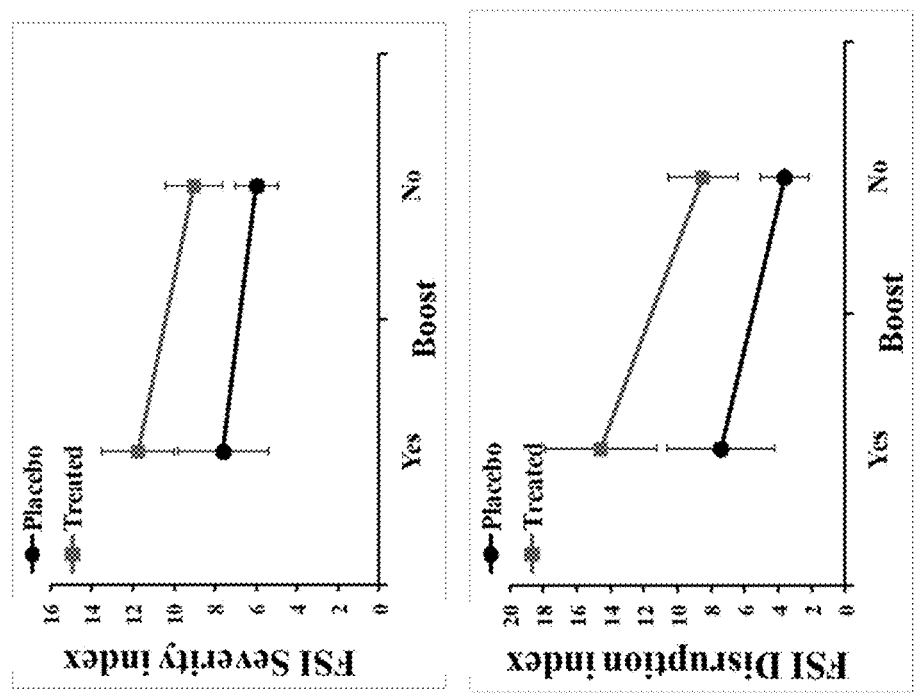
Figure 13A:
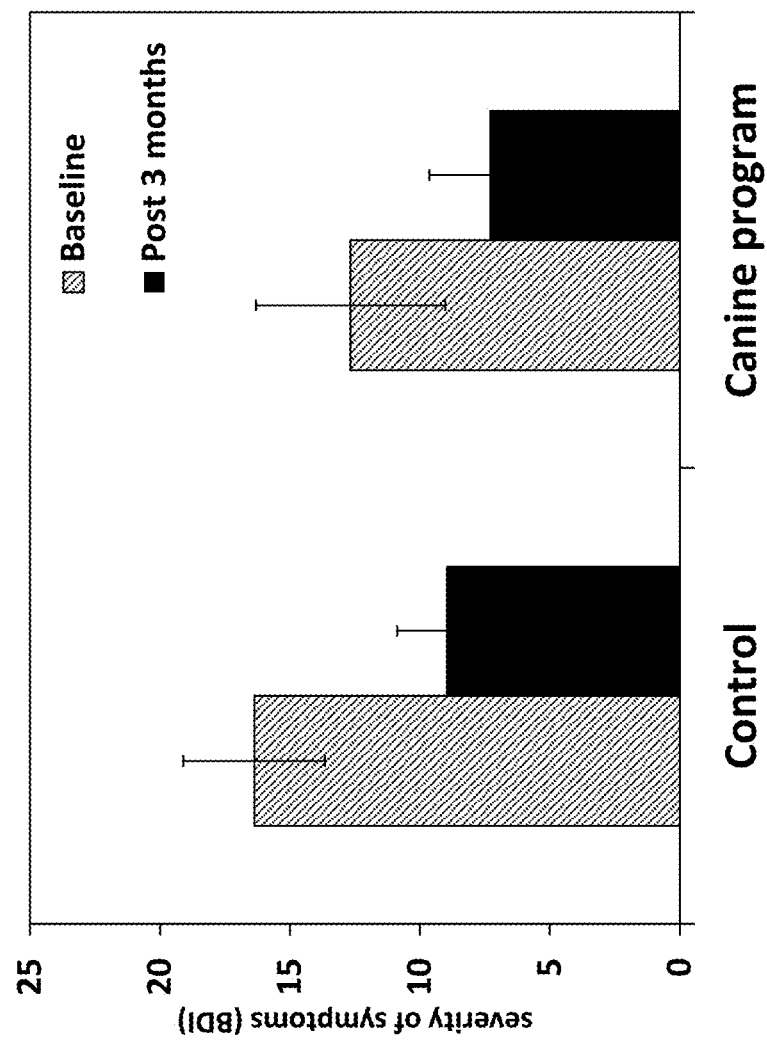
FIGS. 13A-13F show experimental results in a canine-interaction experiment.
Figure 13B:
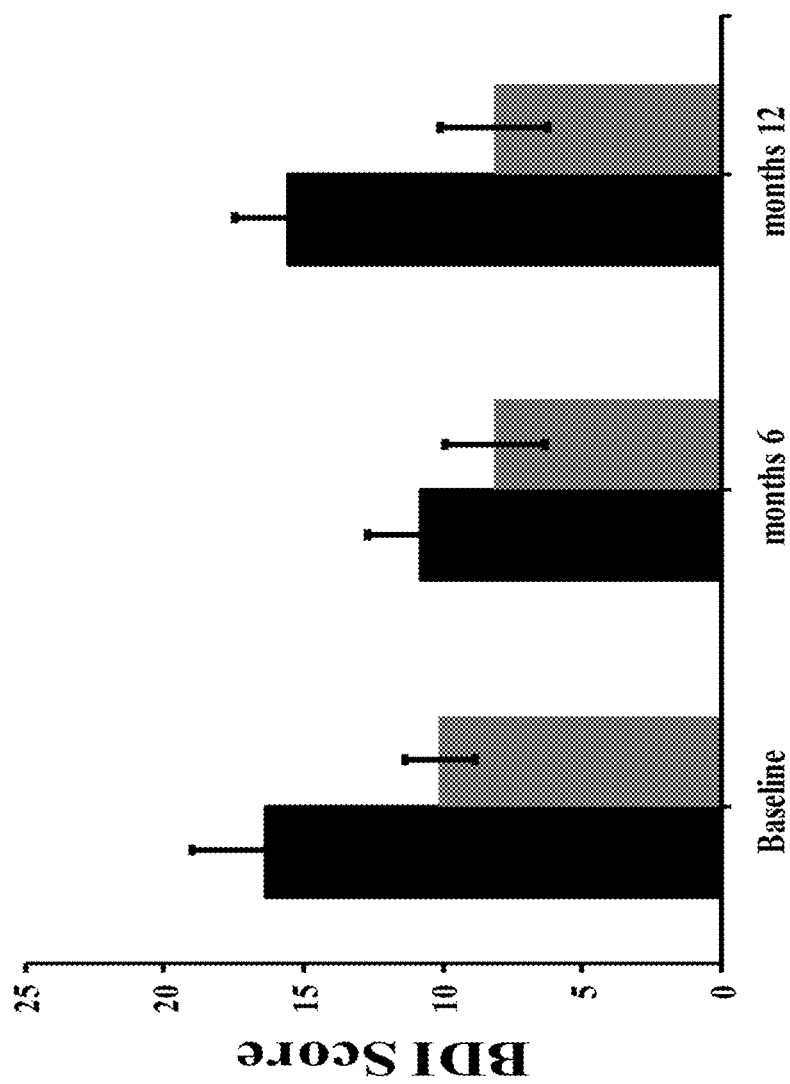
Figure 13C:
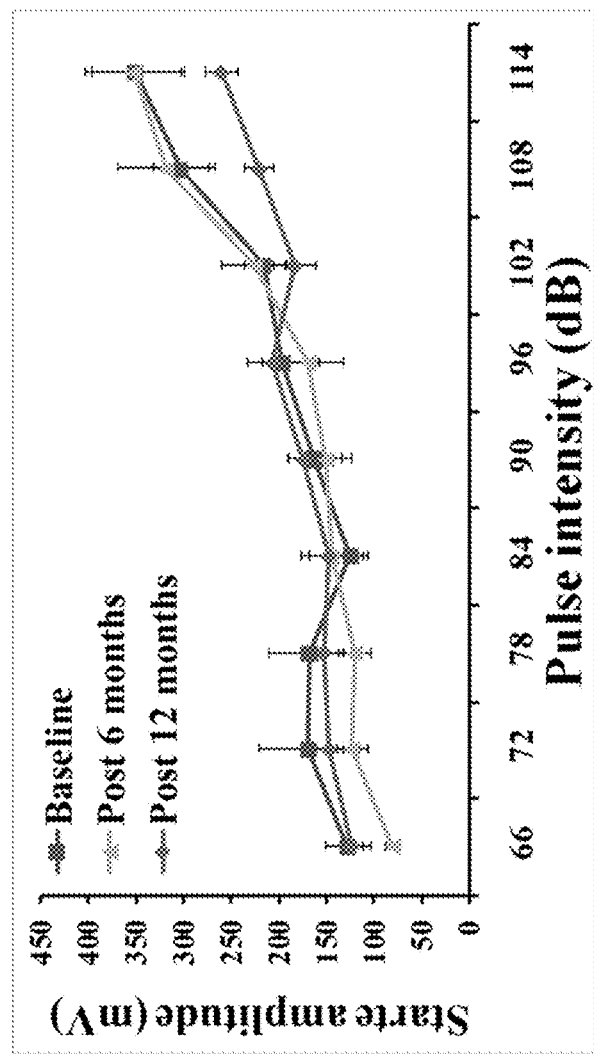
Figure 13D:
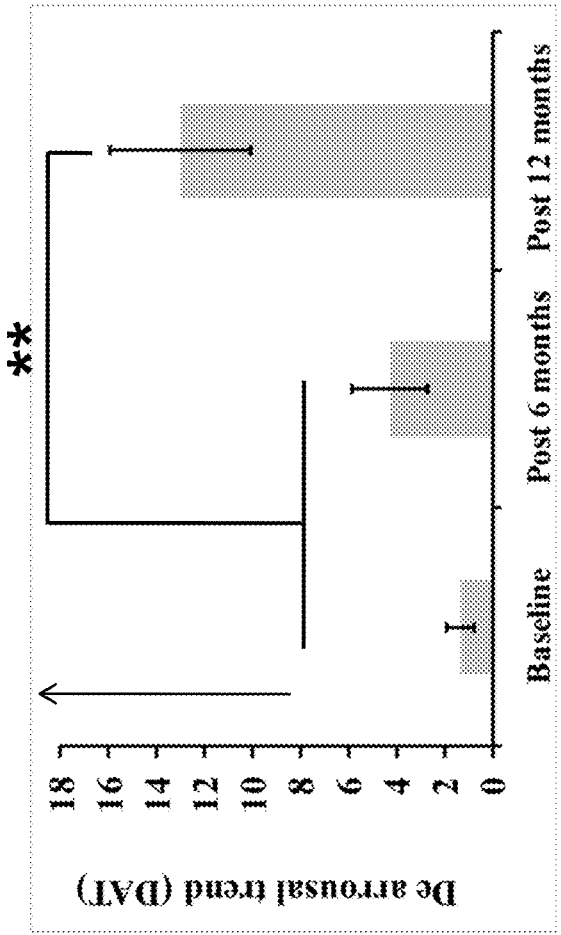
Figure 13D:
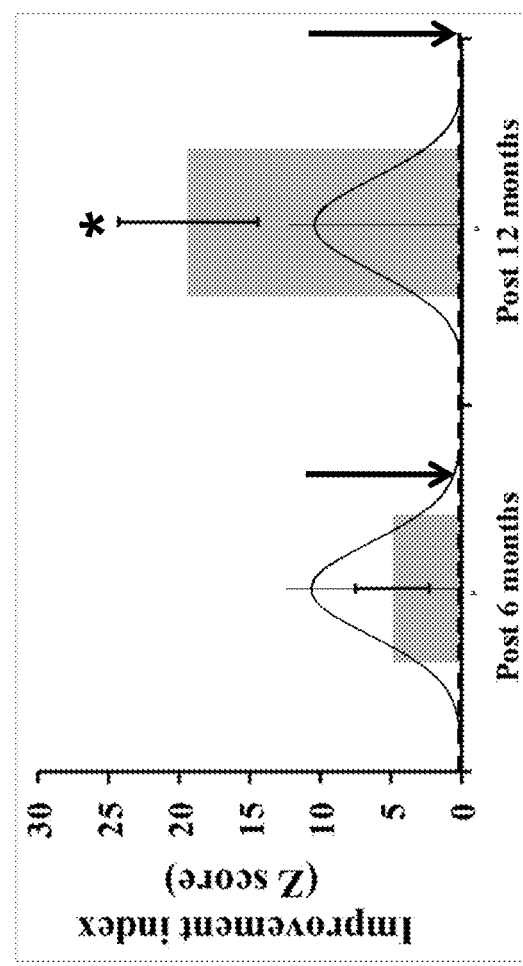
Figure 13E:
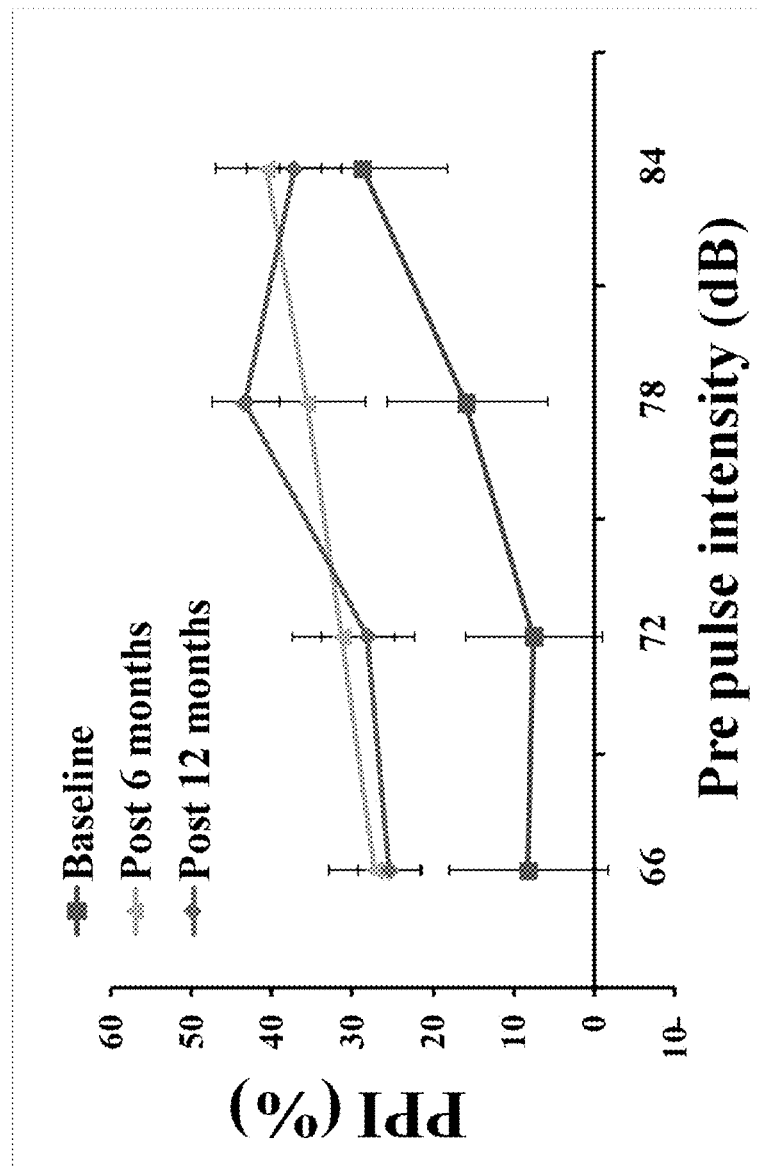
Figure 13F:
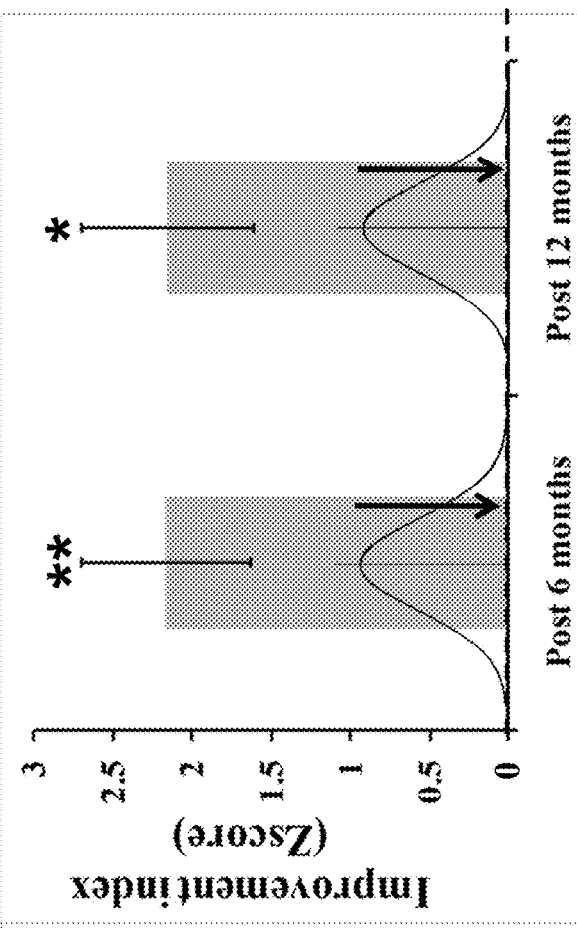
Figure 13F:
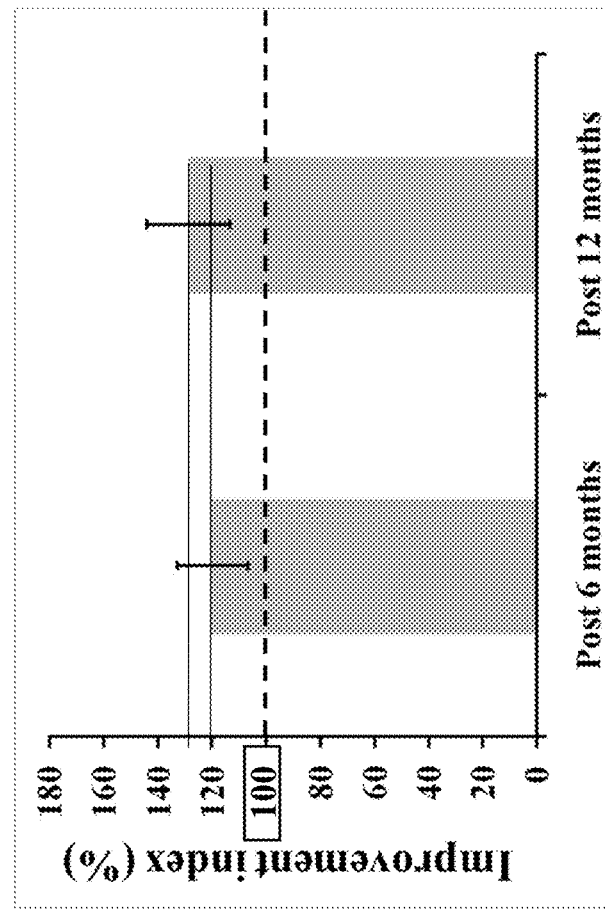

Similarly, it was found that boost did not affect the tendency in the last point of FSI severity (FIG. 9, panel A) or disruption (FIG. 9, panel B). In short, treated group tended to have greater fatigue 4 weeks after the last radiation treatment.

Finally, when it is observed for the startle response as well as for the ASAT, it can also be seen that the tendency is similar for boost versus non boosted treatments in the probability for startle response (FIG. 10, panel A) or startle intensity (FIG. 10, panel B). However, the effect received during the ASAT was significant only women who received boosted treatment (FIG. 10, panel C).

Correlations
Fatigue Symptom Inventory (FSI)

First there was evaluated the correlation between FSI and the clinical diagnosis (FIG. 11), not surprisingly, there was found a good correlation with the fatigue question at all data points. However, there was found that both parameters of FSI correlated at most of the data points (except at 2 weeks) with anxiety. These parameters were positively correlated; it means that higher FSI values were accompanied with higher anxiety levels.

*$P<0.05$; $P<0.01$; *$P<0.001$

When FSI parameters were correlated with the startle and ASAT parameters there was found no significant correlations, thus excluding the possibility of fatigue effects on startle and ASAT analysis. Finally, FSI data was correlated with size, distance (in days) from the last chemotherapy and body mass index (BMI) and found no significant correlations.

Clinical Evaluation

In addition to the significant correlations found between FSI and the clinical data. First, the clinical data (heat waves, elevated fatigue and anxiety impairments in memory, sleep and appetite) was correlated with the startle as well as ASAT data and there was found no significant correlations between the parameters. Next, the clinical data was correlated with tumor size, distance (in days) from the last chemotherapy and body mass index (BMI), there was found a significant correlation between BMI and baseline fatigue level ($R_p=0.369$, $P<0.001$).

Startle and ASAT

Startle response (both eye blink probabilities and startle intensity) as well as ASAT were correlated with tumor size, distance from the last chemo therapy and BMI (FIG. 12), there was found a significant correlation between BMI and startle probabilities at baseline ($Rp=-0.270$, $P<0.046$), as well as 4 weeks post treatment ($Rp=-0.273$, $P<0.042$) as well as startle intensity at baseline ($R_p=-0.294$, $P<0.029$), as well as 2 weeks post treatment ($R_p=-0.366$, $P<0.008$).

Tumor size was significantly and negatively correlated with startle intensity at both baseline ($R_p=-0.320$, $P<0.016$) and 8 weeks post treatment ($R_p=-0.287$, $P<0.032$). Distance from the last chemotherapy was not correlated with any of the startle nor ASAT parameters.

Materials and Methods

Auditory Sustained Attention Test (ASAT)

A computerized human startle response monitoring system (SR-HLAB STARTLE REFLEX, San Diego Instruments, San Diego, Calif.) is used to deliver acoustic startle stimuli via headphones while recording the corresponding electro myographic activity from the orbicularis oculi muscle. Two disposable electrodes (sensor area 12 mm$^2$) are placed approximately 0.75-1 cm below the pupil on the orbicularis oculi muscle and 3rd reference electrode on the mastoid bone. The skin area at the electrode site is prepared using "Skin prep" (3M, Red Dot, Cat. #2236). The session starts with 3 minutes of acclimatization period with 57 dB background noise level that is delivered continuously throughout the session. The session is comprised from 98 pseudo-randomly delivered trails at 10 seconds average Inter-Trial-Interval (ITI, ranging from 6-14 seconds). Forty startle trials comprised of single 30 milliseconds of 96,102, 108,114 dB "pulse alone" startle stimuli to evaluate the startle magnitude and the probability to generate eye blink. Ten "No stimulus" trials were recorded in order to evaluate baseline noise levels. In order to evaluate Pre pulse inhibition (PPI), 40 "pre+pulse" trials consisted from a single 108 dB pulse preceded (100 milliseconds inter-stimulus-interval) by a 20 milliseconds pre-pulse of 9, 15, 21 or 27 dB above background noise (i.e. 66, 72, 78 or 84 dB), in addition to 8 "pre alone" stimuli trials (66, 72, 78 or 84 dB). The PPI is calculated as percent of the habituated/inhibited response as follows: 100−(max response to "pre+pulse" trial/max response to "pulse alone" trial×100; Zubedat, et al, 2014).

Experimental Results—Dog Interactions

The present inventors tested the possible influence of interacting with working dogs on the improvement of PTSD symptoms. The test measured the effects of human-dog interaction on their anxiety and attention capabilities using also physiological measures. The test was conducted on 65 adolescent subjects and 26 dogs aged 24 months on average.

The test was based on:
Caps ca 5 advance questioner, developed by the NMIH for diagnosing PTSD symptoms in adolescents;
BDI: a questioner for depression symptoms;
ASAT: a physiological measurement for sustained attention;
Startle response: a physiological measurement of anxiety, wherein PPI is measured as a reduction of acoustic startle reflexes following the presentation of pre-stimuli;
EDR: a physiological measurement of peripheral arousal/anxiety, wherein the sympathetic nervous system activity is detected by measuring skin conductance change caused by sweating;
Evaluation of handling capabilities (Arcady-Manof); and
Multi-dimensional social observation questioner (Mark Zar-Manof)

During the experiment, in each week, the subjects interacting with the dogs undergo theoretical and practical training for search and rescue operations (home front command). The research contains two groups:
49 future dog-trainers selected for their approach to dogs.
16 subjects which were randomly sampled from other area.

In round 1, 65 subjects participated (16 controls) and went through 3 tests (baseline, 6 months, 12 months). In round 2, 42 students participated (16 controls) and went through 2 tests (baseline, 3 months, 6 months, 9 months and 12 months).

The results are summarized in FIGS. 13A-13E. As can be seen, a significant improvement of the test group was noted in easing PTSD symptoms, a decrease in anxiety, an increase in attention levels and an improvement in the test group's social function in reference to the control group. Detailing the improvement in the different parameters among the students with PTSD is in fact the first, evidence based result for the extent to which working with animals (dogs) improves PTSD symptoms.

Experimental Results—Fighter Pilots

The attention system is highly involved in one's behavior when attention resources allocation is required, in terms of response inhibition and action selection.

A normal human attention system comprises four different anatomically segregated functions:
Sustained attention.
Selective attention.
Orienting of attention.
Executive attention Common current tools to assess attention are based on standard visual paradigms in which series of stimuli are displayed; while measuring subjects' voluntary response as well as no-response (inhibition) to the target and non-target stimuli, respectively. It was previously suggested by the present inventors that reflexive inhibition of response to a startling acoustic pulse following a pre-pulse (i.e., PPI), is modulated by attention functioning. Specifically, it was proposed to be reflected in Auditory sustained attention (ASAT) and an emotional dysregulation Accordingly, the present experiment was intended to investigate the adverse effects of acute sleep deprivation on the Physiologically-measured Auditory Sustained Attention Test (ASAT), and to further evaluate the effects of an accumulated additional partial SD.

Methods

Thirty-five young combat pilots participated in Aero-Medical Center of the Israel Defense Force workshop (Age: 22±2 years).

Figure 14A:
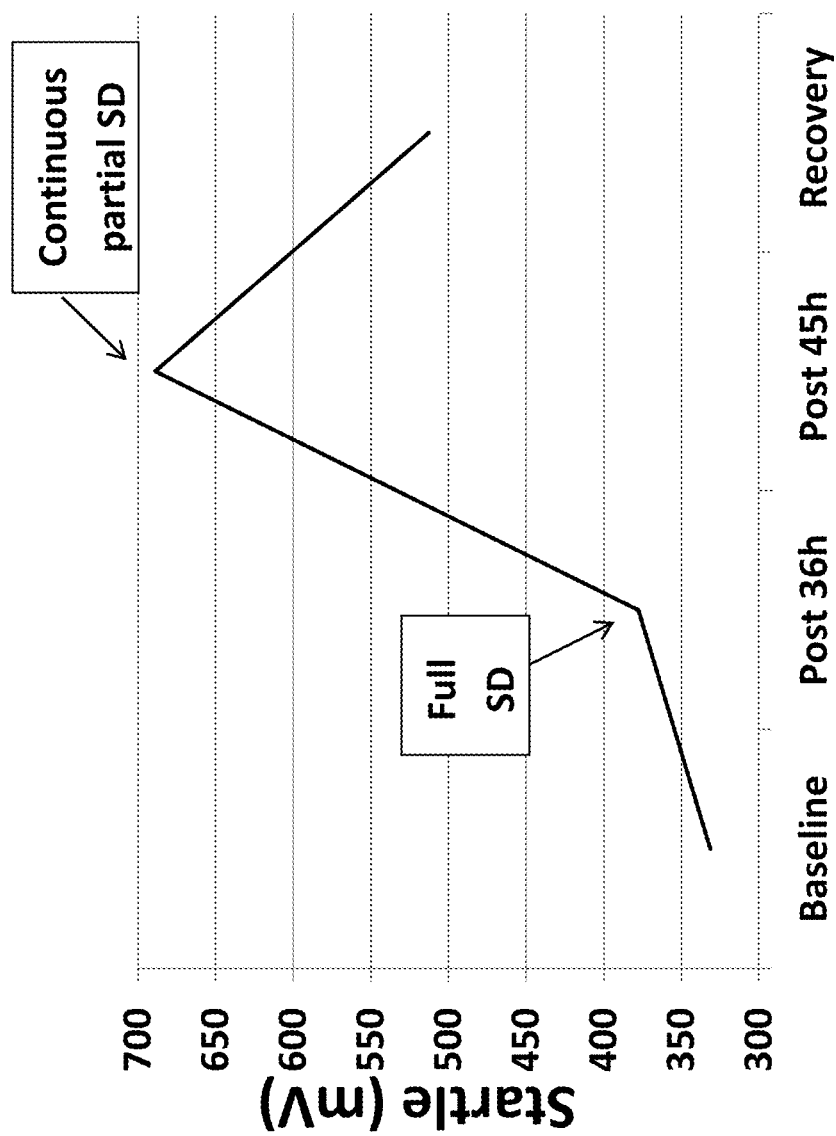
FIGS. 14A-14B show experimental results in combat pilots.
Figure 14B:
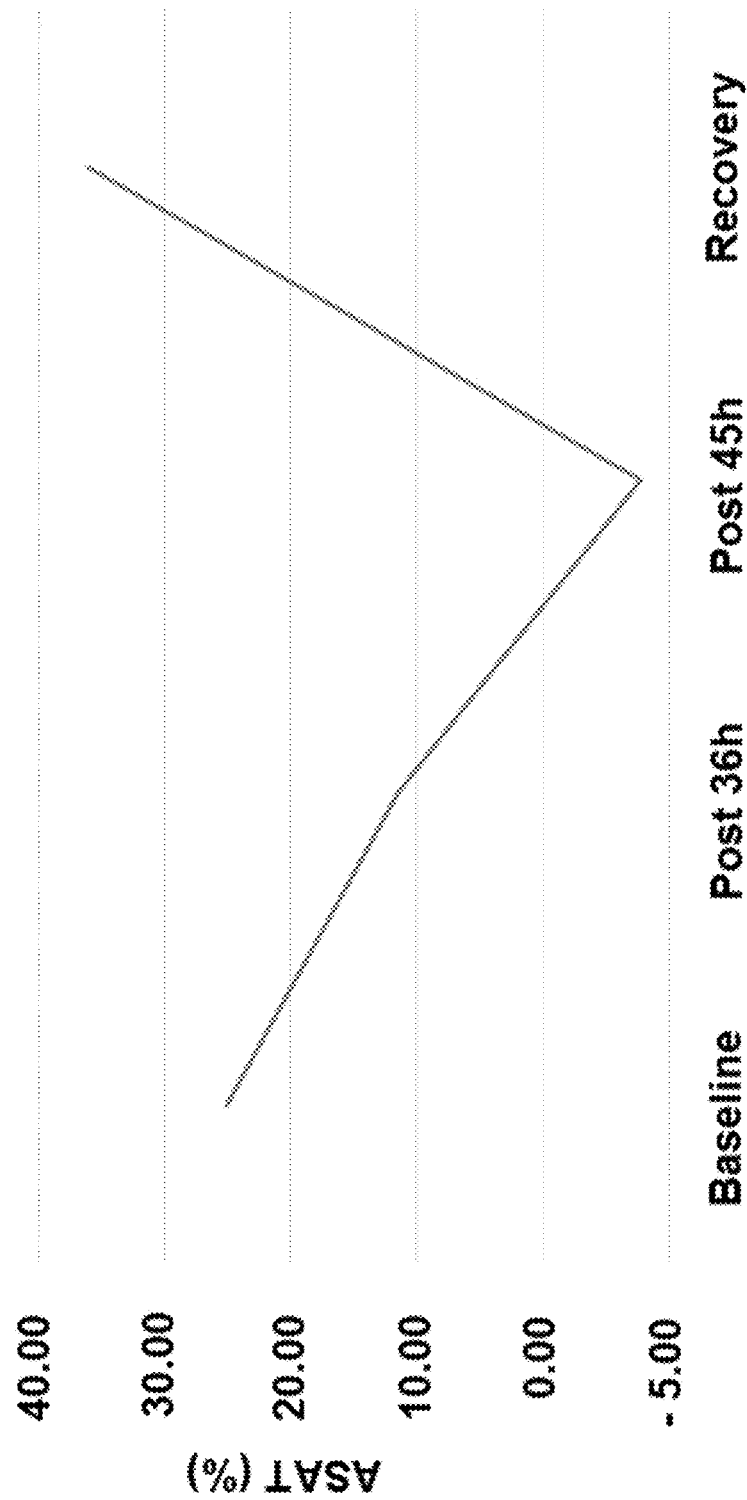

ASAT Measurement Schedule:
Baseline (09:00d1)
Post 22 hrs SD (07:00d2): Complete SD condition.
Post 45 hrs with 3 hrs sleep (06:00d3): Partial SD condition.
Post 72 hrs with >7 hrs night sleep (09:00d4): Recovery
The results are shown in FIGS. 14A-14B.

It may be concluded that attention deficit is associated with dysregulation of multiple systems, including sleep, appetite and sensory perception, thus, the ASAT importance stems from its ability to test the availability of sensorimotor regulating mechanisms as they rely on a much higher velocity response (40-60 ms) compared to the TOVA reaction time (>200 ms) that measures prefrontal executive functions. In a re-testing regimen, the ~10 min ASAT provides an accurate and sensitive measure of attention deficit, executive dysfunction and dysregulation, which are usually addressed separately.

What is claimed is:
1. A method comprising the steps of:
(i) diagnosing or selecting a subject in need of a stimulant attention deficit hyperactivity disorder (ADHD) drug;
(ii) conducting an auditory sustained attention (ASAT) analysis on said subject;

(iii) administering said stimulant ADHD drug to said subject having lower baseline ASAT performance compared to a control value,.

wherein conducting the ASAT analysis comprises:

providing an acoustic background noise;

providing a first acoustic startle stimulus at an intensity higher than the background noise;

providing second acoustic startle stimuli comprising a pre-plus acoustic stimulus and an acoustic startle stimulus; and calculating a Pre-Plus Inhibition (PPI) as a percentage of response inhibition between the first acoustic startle stimulus and the second acoustic startle stimuli; and determining ASAT performance based on the calculated PPI.

2. The method of claim 1, wherein said method confirms or predicts responsiveness of said subject to said stimulant ADHD drug.

3. The method of claim 1, wherein said stimulant ADHD drug is selected from: a short-acting stimulant drug, a long-acting stimulant drug, an intermediate-acting stimulant drug, or any combination thereof.

4. The method of claim 1, wherein said stimulant ADHD drug comprises methylphenidate or any derivative thereof.

5. The method of claim 1, further comprising the step of:

increasing an initial dose of said stimulant ADHD drug to said subject having lower baseline ASAT performance compared to a control value.

6. The method of claim 1, wherein providing the second acoustic startle stimuli comprises providing a predetermined inter-stimulus-interval between the pre-plus acoustic stimulus and the acoustic startle stimulus.

* * * * *